United States Patent
Amigo et al.

(10) Patent No.: US 10,410,293 B2
(45) Date of Patent: *Sep. 10, 2019

(54) SENSOR SYSTEMS AND METHODS FOR SENSOR-BASED ACTIVITY EVALUATION

(71) Applicant: Hartford Fire Insurance Company, Hartford, CT (US)

(72) Inventors: Andrew J. Amigo, Essex, MA (US); Michael Gingrave, Wethersfield, CT (US)

(73) Assignee: Hartford Fire Insurance Company, Hartford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/190,851

(22) Filed: Nov. 14, 2018

(65) Prior Publication Data

US 2019/0080417 A1    Mar. 14, 2019

Related U.S. Application Data

(63) Continuation of application No. 15/018,438, filed on Feb. 8, 2016, now Pat. No. 10,140,663, which is a
(Continued)

(51) Int. Cl.
*G06Q 40/08* (2012.01)
*A61B 5/103* (2006.01)
(Continued)

(52) U.S. Cl.
CPC .......... *G06Q 40/08* (2013.01); *A61B 5/1038* (2013.01); *A61B 5/112* (2013.01); *A61B 5/1112* (2013.01);
(Continued)

(58) Field of Classification Search
None
See application file for complete search history.

(56) References Cited

U.S. PATENT DOCUMENTS 3,972,320 A    8/1976   Kalman
4,444,205 A *  4/1984   Jackson ............... A61B 5/1106
                                                338/114
(Continued)

FOREIGN PATENT DOCUMENTS

WO    2006042415 A1    4/2006
WO    2008097499 A1    8/2008

OTHER PUBLICATIONS

International Search Report dated May 6, 2008 in related PCT Application No. PCT/US2008/001435. Pursuant to 37 C.F.R. § 1.98(d) and MPEP 609.02, this reference is not required to be submitted because a copy was previously submitted in U.S. Appl. No. 15/018,438, which is relied upon for an earlier effective filing date under 35 U.S.C. 120.

(Continued)

*Primary Examiner* — Curtis J King
(74) *Attorney, Agent, or Firm* — Howard IP Law Group, P.C.

(57) ABSTRACT

Systems and methods are discussed for providing sensor enhanced safety, recovery, and activity evaluation systems. Sensors that monitor user activity and behavior are worn by a user and/or placed in the user environment. Data from the sensors are processed to obtain a safety, recovery, and/or activity evaluation. Based on the evaluation, recommendations or adjustments to the terms of an insurance policy covering the user, the user's employer, or a facility providing health care to the user to accurately reflect the risks associated with the user, employer, and/or facility. In embodiments, an alert may be generated when a failure to conform with activity guidelines is detected.

16 Claims, 10 Drawing Sheets

Related U.S. Application Data continuation of application No. 14/143,941, filed on Dec. 30, 2013, now Pat. No. 9,256,906, which is a continuation of application No. 12/793,301, filed on Jun. 3, 2010, now Pat. No. 8,638,228, which is a continuation-in-part of application No. 12/362,737, filed on Jan. 30, 2009, now Pat. No. 8,149,126, which is a continuation-in-part of application No. 12/024,676, filed on Feb. 1, 2008, now Pat. No. 9,563,919.

(60) Provisional application No. 60/899,076, filed on Feb. 2, 2007.

(51) Int. Cl.
    *A61B 5/11*     (2006.01)
    *A61B 5/00*     (2006.01)
    *G06Q 10/10*     (2012.01)
    *G16H 50/30*     (2018.01)
    *G06F 19/00*     (2018.01)

(52) U.S. Cl.
CPC .......... *A61B 5/1115* (2013.01); *A61B 5/1118* (2013.01); *A61B 5/1121* (2013.01); *A61B 5/1123* (2013.01); *A61B 5/6804* (2013.01); *G06F 19/00* (2013.01); *G06Q 10/105* (2013.01); *G16H 50/30* (2018.01); *A61B 5/6807* (2013.01); *A61B 2503/20* (2013.01)

(56) References Cited

U.S. PATENT DOCUMENTS

| | | | |
|---|---|---|---|
| 4,665,388 A | 5/1987 | Ivie et al. | |
| 4,665,928 A * | 5/1987 | Linial | A61B 5/1121 482/1 |
| 4,798,197 A * | 1/1989 | Nippoldt | A61H 1/02 601/34 |
| 4,831,526 A | 5/1989 | Luchs et al. | |
| 4,938,476 A | 7/1990 | Brunelle et al. | |
| 4,993,428 A | 2/1991 | Arms | |
| 5,164,707 A | 11/1992 | Rasmussen et al. | |
| 5,269,318 A | 12/1993 | Nashner | |
| 5,271,416 A | 12/1993 | Lepley | |
| 5,289,318 A | 2/1994 | Sekine et al. | |
| 5,497,147 A | 3/1996 | Arms et al. | |
| 5,570,301 A | 10/1996 | Barrus | |
| 5,621,667 A | 4/1997 | Waters | |
| 5,777,467 A | 7/1998 | Arms et al. | |
| 5,825,283 A | 10/1998 | Camhi et al. | |
| 5,877,707 A | 3/1999 | Kowalick | |
| 5,887,351 A | 3/1999 | Arms et al. | |
| 6,025,782 A | 2/2000 | Newham | |
| 6,059,576 A | 5/2000 | Brann | |
| 6,073,043 A * | 6/2000 | Schneider | A61B 5/06 128/899 |
| 6,119,516 A * | 9/2000 | Hock | A61B 5/1121 600/547 |
| 6,174,294 B1 | 1/2001 | Crabb et al. | |
| 6,236,973 B1 | 5/2001 | Dillard | |
| 6,339,745 B1 | 1/2002 | Novik | |
| 6,398,740 B1 | 6/2002 | Lavery et al. | |
| 6,433,629 B2 | 8/2002 | Hamel et al. | |
| 6,499,368 B2 | 12/2002 | Arms et al. | |
| 6,529,127 B2 | 3/2003 | Townsend et al. | |
| 6,573,831 B2 | 6/2003 | Ikeda et al. | |
| 6,588,282 B2 | 7/2003 | Arms | |
| 6,589,055 B2 | 7/2003 | Osborne et al. | |
| 6,622,567 B1 | 9/2003 | Hamel et al. | |
| 6,714,763 B2 | 3/2004 | Hamel et al. | |
| 6,828,779 B2 | 12/2004 | Townsend et al. | |
| 6,834,436 B2 | 12/2004 | Townsend et al. | |
| 6,868,386 B1 * | 3/2005 | Henderson | G06Q 30/0283 340/439 |
| 6,871,413 B1 | 3/2005 | Arms | |
| 6,901,654 B2 | 6/2005 | Arms et al. | |
| 7,061,229 B2 | 6/2006 | Townsend et al. | |
| 7,081,693 B2 | 7/2006 | Hamel et al. | |
| 7,143,004 B2 | 11/2006 | Townsend et al. | |
| 7,170,201 B2 | 1/2007 | Hamel et al. | |
| 7,210,240 B2 * | 5/2007 | Townsend | A61B 5/1116 33/341 |
| 7,256,505 B2 | 8/2007 | Arms et al. | |
| 7,256,695 B2 | 8/2007 | Hamel et al. | |
| 7,361,998 B2 | 4/2008 | Hamel et al. | |
| 7,387,607 B2 | 6/2008 | Holt et al. | |
| 7,429,805 B2 | 9/2008 | Hamel et al. | |
| 7,433,798 B2 | 10/2008 | Townsend et al. | |
| 7,461,560 B2 | 12/2008 | Arms et al. | |
| 7,591,187 B2 | 9/2009 | Hamel | |
| 7,639,135 B2 | 12/2009 | Arms et al. | |
| 7,646,135 B1 | 1/2010 | Churchill et al. | |
| 7,652,582 B2 | 1/2010 | Littell | |
| 7,668,667 B2 | 2/2010 | Robb et al. | |
| 7,672,781 B2 | 3/2010 | Churchill et al. | |
| 7,692,365 B2 | 4/2010 | Churchill et al. | |
| 7,695,282 B2 | 4/2010 | Lanktree | |
| 7,696,621 B2 | 4/2010 | Arms et al. | |
| 7,698,830 B2 | 4/2010 | Townsend et al. | |
| 7,712,365 B1 | 5/2010 | James | |
| 7,719,416 B2 | 5/2010 | Arms et al. | |
| 7,747,415 B1 | 6/2010 | Churchill et al. | |
| 8,392,221 B1 * | 3/2013 | Milanovich | G06Q 40/08 705/4 |
| 8,521,546 B2 | 8/2013 | Brown | |
| 8,831,299 B2 | 9/2014 | Kurtz et al. | |
| 2002/0013717 A1 * | 1/2002 | Ando | A61B 5/0002 705/4 |
| 2002/0120472 A1 * | 8/2002 | Dvorak | G06Q 50/24 705/3 |
| 2002/0143277 A1 * | 10/2002 | Wood | A61B 5/1071 600/595 |
| 2003/0158758 A1 * | 8/2003 | Kanazawa | G06Q 40/02 705/4 |
| 2003/0171659 A1 | 9/2003 | Dean | |
| 2003/0171956 A1 | 9/2003 | Cox et al. | |
| 2003/0210149 A1 | 11/2003 | Reisman et al. | |
| 2004/0010420 A1 * | 1/2004 | Rooks | G06F 19/3481 705/2 |
| 2004/0100384 A1 | 5/2004 | Chen et al. | |
| 2004/0183684 A1 | 9/2004 | Callaway | |
| 2004/0199056 A1 * | 10/2004 | Husemann | A61B 5/0002 600/300 |
| 2004/0230138 A1 | 11/2004 | Inoue et al. | |
| 2005/0020409 A1 * | 1/2005 | Hayamizu | G09B 19/0038 482/51 |
| 2005/0055248 A1 | 3/2005 | Helitzer et al. | |
| 2005/0093537 A1 | 5/2005 | Townsend et al. | |
| 2005/0102172 A1 * | 5/2005 | Sirmans, Jr. | G06Q 40/02 705/4 |
| 2005/0105231 A1 | 5/2005 | Hamel et al. | |
| 2005/0116544 A1 | 6/2005 | Hamel et al. | |
| 2005/0116545 A1 | 6/2005 | Hamel et al. | |
| 2005/0140212 A1 | 6/2005 | Hamel et al. | |
| 2005/0146220 A1 | 7/2005 | Hamel et al. | |
| 2005/0288968 A1 * | 12/2005 | Collins | G06F 19/328 705/4 |
| 2006/0033625 A1 | 2/2006 | Johnson et al. | |
| 2006/0064320 A1 * | 3/2006 | Postrel | G06F 19/00 705/2 |
| 2006/0078853 A1 | 4/2006 | Lanktree | |
| 2006/0080146 A1 * | 4/2006 | Cook | G06Q 10/00 705/2 |
| 2006/0103534 A1 | 5/2006 | Arms et al. | |
| 2006/0111944 A1 * | 5/2006 | Sirmans, Jr. | G06Q 30/0209 705/3 |
| 2006/0247504 A1 | 11/2006 | Tice | |
| 2006/0247953 A1 * | 11/2006 | Pollack | G06Q 40/08 705/4 |
| 2006/0253306 A1 * | 11/2006 | Richardson | G06Q 10/1057 705/4 |
| 2006/0273894 A1 | 12/2006 | Goehler | |
| 2006/0282017 A1 | 12/2006 | Avni et al. | |

(56) References Cited

U.S. PATENT DOCUMENTS

| | | |
|---|---|---|
| 2007/0005404 A1 | 1/2007 | Raz et al. |
| 2007/0016542 A1* | 1/2007 | Rosauer ............... G06N 5/022 |
| | | 706/21 |
| 2007/0027726 A1 | 2/2007 | Warren et al. |
| 2007/0117680 A1 | 5/2007 | Neff et al. |
| 2007/0169364 A1 | 7/2007 | Townsend et al. |
| 2007/0177651 A1 | 8/2007 | Daugherty et al. |
| 2007/0250286 A1 | 10/2007 | Duncan et al. |
| 2007/0250352 A1* | 10/2007 | Tawil ................. G06Q 10/10 |
| | | 705/4 |
| 2007/0265888 A1* | 11/2007 | Castelli ............... G06F 19/328 |
| | | 705/4 |
| 2007/0285248 A1 | 12/2007 | Hamel et al. |
| 2008/0021834 A1 | 1/2008 | Holla et al. |
| 2008/0125289 A1 | 5/2008 | Pryor et al. |
| 2008/0154653 A1* | 6/2008 | Goux .................. G06Q 10/10 |
| | | 705/4 |
| 2008/0189142 A1* | 8/2008 | Brown ................ G06Q 10/00 |
| | | 705/4 |
| 2008/0288020 A1* | 11/2008 | Einav ................. A61N 1/36003 |
| | | 607/48 |
| 2008/0294012 A1 | 11/2008 | Kurtz et al. |
| 2009/0089103 A1 | 4/2009 | Chien et al. |
| 2009/0150191 A1* | 6/2009 | Roschelle ............ G06Q 10/10 |
| | | 705/4 |
| 2009/0210257 A1* | 8/2009 | Chalfant ............. G06Q 40/08 |
| | | 705/4 |
| 2009/0235009 A1 | 9/2009 | Chiu |
| 2009/0322557 A1 | 12/2009 | Robb et al. |
| 2010/0063778 A1 | 3/2010 | Schrock et al. |
| 2010/0152621 A1* | 6/2010 | Janna ................. A61B 5/0031 |
| | | 600/595 |
| 2010/0234182 A1* | 9/2010 | Hoffman ............. A61B 5/1125 |
| | | 482/8 |
| 2011/0004076 A1* | 1/2011 | Janna ................. A61B 5/0031 |
| | | 600/302 |
| 2011/0021318 A1* | 1/2011 | Lumsden ............ A63B 69/00 |
| | | 482/8 |
| 2011/0040572 A1* | 2/2011 | Chmiel ............... A61B 5/0002 |
| | | 705/2 |
| 2011/0046519 A1* | 2/2011 | Raheman ............ A61B 5/112 |
| | | 600/595 |
| 2011/0087137 A1* | 4/2011 | Hanoun .............. A61B 5/0205 |
| | | 600/587 |
| 2011/0112970 A1* | 5/2011 | Yu ..................... G06F 21/6254 |
| | | 705/51 |
| 2011/0131060 A1* | 6/2011 | Schuster ............. G06Q 10/10 |
| | | 705/3 |
| 2011/0160544 A1* | 6/2011 | Hayter ................ A61B 5/4833 |
| | | 600/300 |
| 2011/0161100 A1* | 6/2011 | Peak .................. G06Q 40/08 |
| | | 705/2 |
| 2011/0191158 A1 | 8/2011 | Kateraas et al. |
| 2011/0213218 A1* | 9/2011 | Weiner ............... A61B 5/0002 |
| | | 600/301 |
| 2012/0116548 A1 | 5/2012 | Goree et al. |
| 2012/0158436 A1 | 6/2012 | Bauer et al. |
| 2012/0172675 A1* | 7/2012 | Thomas .............. G16H 15/00 |
| | | 600/300 |
| 2012/0220428 A1* | 8/2012 | Carlson .............. A63B 21/023 |
| | | 482/8 |
| 2012/0221254 A1* | 8/2012 | Kateraas ............ A61B 5/02055 |
| | | 702/19 |
| 2013/0009993 A1* | 1/2013 | Horseman ........... G06F 19/3418 |
| | | 345/633 |
| 2013/0096932 A1* | 4/2013 | Saidel ................ G06Q 10/10 |
| | | 705/2 |
| 2013/0108995 A1 | 5/2013 | DePasqua et al. |
| 2013/0128022 A1* | 5/2013 | Bose .................. H04N 7/18 |
| | | 348/77 |
| 2013/0225309 A1 | 8/2013 | Bentley et al. |
| 2013/0310658 A1 | 11/2013 | Ricks et al. |
| 2013/0332286 A1 | 12/2013 | Medelius et al. |
| 2014/0266630 A1 | 9/2014 | Beckman |
| 2014/0372133 A1 | 12/2014 | Austrum et al. |

OTHER PUBLICATIONS

Luinge et al., Measuring orientation of human body segments using miniature gyroscopes and accelerometers, Med. Biol. Eng. Comput., 2005, 43, 273-282. Pursuant to 37 C.F.R. § 1.98(d) and MPEP 609.02, this reference is not required to be submitted because a copy was previously submitted in U.S. Appl. No. 15/018,438, which is relied upon for an earlier effective filing date under 35 U.S.C. 120.

Ellegast, R. et al., "Load weight determination during dynamic working procedures using the pedar foot pressure distribution measuring system", Clin Biomech (Bristol, Avon), Apr. 12, 1997, 2 pages. Pursuant to 37 C.F.R. § 1.98(d) and MPEP 609.02, this reference is not required to be submitted because a copy was previously submitted in U.S. Appl. No. 15/018,438, which is relied upon for an earlier effective filing date under 35 U.S.C. 120.

Lavender, Steven, "Training in lifting", Professional Safety 47.12, Dec. 2002 : 30-35. Pursuant to 37 C.F.R. § 1.98(d) and MPEP 609.02, this reference is not required to be submitted because a copy was previously submitted in U.S. Appl. No. 15/018,438, which is relied upon for an earlier effective filed under 35 U.S.C. 120.

McLean, Robert B., Accomodations in Lifting Technique due to Local and General Fatigue by a Low Back Pain Population, 2003, 191 pages. Pursuant to 37 C.F.R. § 1.98(d) and MPEP 609.02, this reference is not required to be submitted because a copy was previously submitted in U.S. Appl. No. 15/018,438, which is relied upon for an earlier effective filed under 35 U.S.C. 120.

Mini Mitter Co., Inc., "VitalSense®—Wireless vital signs monitoring", Oct. 11, 2004, 4 pages. Pursuant to 37 C.F.R. § 1.98(d) and MPEP 609.02, this reference is not required to be submitted because a copy was previously submitted in U.S. Appl. No. 15/018,438, which is relied upon for an earlier effective filed under 35 U.S.C. 120.

\* cited by examiner

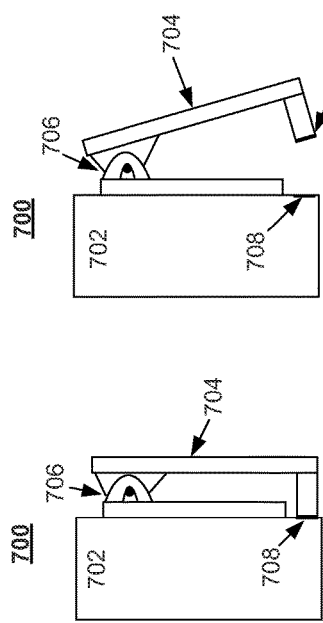
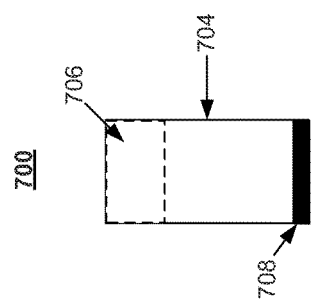
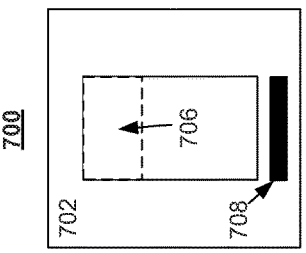
FIG. 7A
FIG. 7B
FIG. 7C
FIG. 7D

US 10,410,293 B2

SENSOR SYSTEMS AND METHODS FOR SENSOR-BASED ACTIVITY EVALUATION

CROSS-REFERENCE TO RELATED APPLICATIONS

This application is a continuation application of co-pending U.S. patent application Ser. No. 15/018,438, filed Feb. 8, 2016, which is a continuation application of U.S. patent application Ser. No. 14/143,941, filed Dec. 30, 2013, now U.S. Pat. No. 9,256,906, which is a continuation application of U.S. patent application Ser. No. 12/793,301, filed Jun. 3, 2010, now U.S. Pat. No. 8,638,228, which is a continuation-in-part of U.S. patent application Ser. No. 12/362,737, filed Jan. 30, 2009, now U.S. Pat. No. 8,149,126, which is a continuation-in-part of U.S. patent application Ser. No. 12/024,676, filed Feb. 1, 2008, now U.S. Pat. No. 9,563,919, which claims the benefit of U.S. Provisional Application No. 60/899,076, filed Feb. 2, 2007, the entire contents of all of which are hereby incorporated herein by reference for all purposes.

BACKGROUND OF THE INVENTION

Many insurance companies are considering offering, or do offer, discounts or variable pricing for automobile insurance based on data collected from vehicle telematics. Safety in the workplace includes perils beyond driving, including environmental conditions, physical stress and strain, and dangerous equipment. Sensors on the marketplace and in development can identify dangerous scenarios, including environmental conditions, worker behaviors, use or lack of use of proper safety equipment, and interactions with dangerous machines, substances or areas.

Workers' compensation insurance provides compensation for workers that are injured on the job. This compensation may include medical expenses, death benefits, and payments in lieu of lost wages. Workers' compensation insurance is state-mandated for most employees and is generally provided by private insurance companies, though some states operate a state fund.

Rates for workers' compensation insurance are set by state and are based on industry and job classification. Workers' compensation rating starts with a base rate, derived for each of some 600 classifications. This base rate is not modified for the smallest businesses, but for others, it is. These modifications include a mandatory application of an experience rating credit or debit, depending on a business's claims history compared to the average in that business class. Also, discretionary pricing modifications can be applied by the carrier depending on its underwriting evaluation of the account. Many large accounts share in the funding of their claims via large deductibles, policyholder dividends and retrospectively rated programs. These kinds of programs are generally referred to as "risk share" plans. For those businesses that are subject to experience rating or a "risk share" plan, their net cost of workers' compensation insurance is decreased to the extent they can either prevent, or mitigate the value of, claims.

Most insurance carriers that sell workers' compensation insurance provide professional services that help businesses prevent or mitigate the values of claims, primarily by reviewing the business's exposures and current controls, and by assessing the causes of prior claims and subsequently recommending and implementing solutions. Again, to the extent that these solutions reduce the number and dollar amount of claims, overall, the premium paid by the business will also be reduced. Loss control services are generally available to all businesses, but are most cost-effective for larger businesses.

Typically, loss control services are part of the basic product sold by an insurance carrier. However, loss control services may be made more effective and efficient by appropriately utilizing technology. In particular, sensor technologies that allow insured businesses to quickly identify unsafe situations, thereby providing the businesses with opportunity to correct them, and technologies that give insurance carriers automatic feedback and information on the safety performance of their policyholders, may beneficially contribute to a streamlined workers' compensation insurance evaluation system and advantageously decrease the risk of accidents in the workplace. In addition to streamlining workers' compensation insurance evaluation systems, sensor technologies may assist in improving risk evaluation and loss control for other types of insurance, such as group, short or long-term disability insurance, professional or general liability insurance, and/or medical malpractice insurance. These sensor technologies may also be used to monitor and facilitate other aspects of insured entities, such as general employee health, post-injury return-to-work programs for injured employees, and the activity levels of patients in a healthcare facility.

SUMMARY OF THE INVENTION

Accordingly, in one aspect the invention relates to an activity evaluation system for managing an insurance-related process. The system comprises at least one sensor, a data store, an activity evaluation module, a communications module, and a business computer processor. The sensor(s) are configured to monitor the activity of an individual associated with an insured entity. The data store stores demographic information about the individual. In certain embodiments, the demographic information about the individual comprises one or more of height, age, weight, and stride length of the individual. The activity evaluation module is configured to collect data from the sensor(s), analyze the data to determine activity characteristics, and output an activity evaluation based on the activity characteristics and the demographic information. The communications module may communicate the collected data and/or the recovery evaluation to a server operated by an insurance company insuring the entity. The business computer processor is configured to adjust a term of an insurance policy covering the insured entity based on the activity evaluation. The term to be adjusted includes a premium, a deductible, a limit, services associated with the insurance policy, costs of the services, rating plan parameters, and/or dividend plan parameters.

In some embodiments, the system includes an output device configured to provide an insurance recommendation to the individual and/or the insured entity based at least in part on the activity evaluation. The insurance recommendation may comprise one of a loss-control recommendation, an exposure management recommendation, an insurance risk evaluation recommendation, an underwriting workflow recommendation, and a claims management workflows recommendation. In one aspect, the insurance recommendation comprises a loss-control recommendation, and the loss-control recommendation comprises one or more of a patient intake decision for the individual, an initial diagnosis for the individual, care instructions for the individual, a patient progress determination for the individual, a determination of sufficient activity for the individual, and a determination of activity conformance for the individual. In another aspect the individual is an employee, and the loss-control recommendation comprises the determination of sufficient activity for the individual to determine if the individual is healthy, and adjusting the term of the insurance policy comprises adjusting a workers compensation premium associated with the insured entity. In some embodiments, the individual is an employee recovering from an injury, and the loss-control recommendation comprises the determination of activity conformance for the individual based on the activity evaluation being indicative of the individual's activity conforming to one of prescribed activity guidelines and personalized threshold guidelines applicable to the individual. In other embodiments, the individual is a patient, and the loss-control recommendation comprises the determination of sufficient activity for the individual based on the activity evaluation being indicative of the individual's activity conforming to one or more of ulcer prevention movement guidelines, prescribed movement guidelines, activity guidelines, and movement threshold guidelines applicable to the individual.

In another aspect, the invention relates to a activity evaluation system for use in managing an insurance-related process. The system includes at least one sensor, a data store, an activity evaluation module, a communications module, and a business computer processor. The at least one sensor is configured to monitor activity of a plurality of individuals associated and distinct from an insured entity. The data store stores demographic information about the individuals. The activity evaluation module is configured to collect data from the sensor(s), analyze the data to determine activity characteristics, and output an activity evaluation based on the activity characteristics and the demographic information. The communications module may communicate the collected data and/or the activity evaluation to a server operated by an insurance company insuring the entity. The business computer processor is configured to adjust a workers compensation premium of an insurance policy covering the insured entity based on the activity evaluation, so as to provide an adjustment favorable to the insured entity responsive to the activity evaluation being indicative of healthy activity by the plurality of individuals.

In some embodiments, the system includes an output device configured to provide an insurance recommendation to the individual and/or the insured entity based at least in part on the activity evaluation. The insurance recommendation may comprise one of a loss-control recommendation to institute policies to promote healthy activity.

In other aspects, the invention relates to methods for using and implementing the system described above.

BRIEF DESCRIPTION OF THE FIGURES

FIGS. 7A-D depict various views of a wearable sensor, according to an illustrative embodiment of the invention;

DETAILED DESCRIPTION

To provide an overall understanding of the invention, certain illustrative embodiments will now be described. However, it will be understood by one of ordinary skill in the art that the methods described herein may be adapted and modified as is appropriate for the application being addressed and that the systems and methods described herein may be employed in other suitable applications, and that such other additions and modifications will not depart from the scope hereof.

Figure 1:
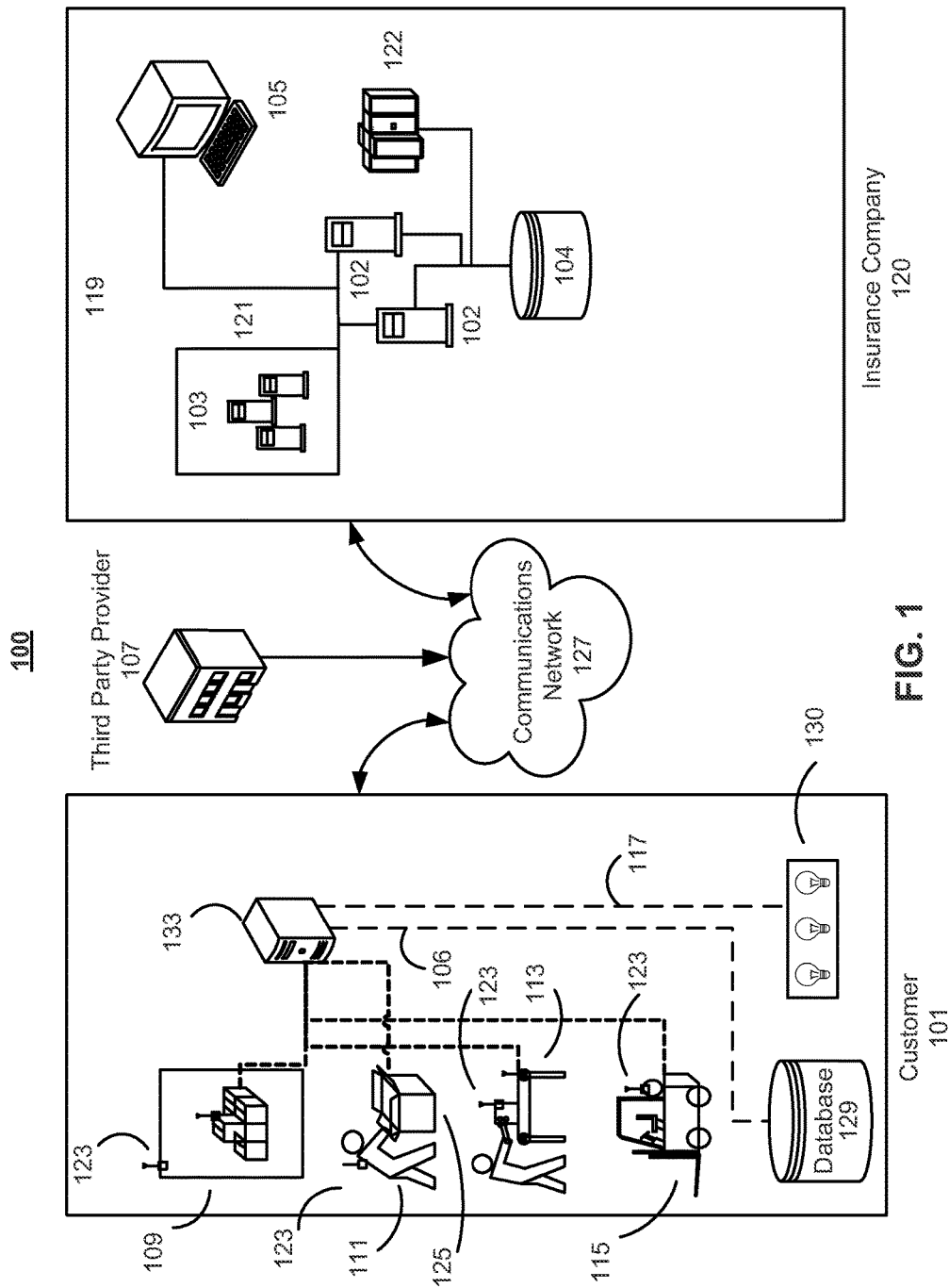
FIG. 1 is a schematic diagram of a system suitable for monitoring, evaluating, and providing feedback on employee workplace safety, according to an illustrative embodiment of the invention.

FIG. 1 is a schematic diagram of a system 100 for monitoring, evaluating, and providing feedback on employee workplace safety at an insured entity. In FIG. 1, insurance company 120 provides customer 101 with insurance coverage. The type of insurance provided by insurance company 120 may be any type of insurance, such as group, short or long-term disability insurance, professional or general liability insurance, medical malpractice insurance, and/or workers' compensation insurance. Customer 101 employs one or more employees 111. Employees 111 work at a workplace environment 109 that is affiliated with customer 101. Workplace environment 109 may include one or more facilities located together or separately from each other. Workplace environment 109 may not be at a fixed location, such as when customer 101 is a contractor who travels to various locations for work. Insurance company 120 can simultaneously provide services to multiple customers, although only one customer 101 is shown in FIG. 1 for clarity.

While on the job, employees 111 may have accidents or develop chronic ailments as a result of handling various types of hazardous machinery 113, equipment 115, and objects 125. A hazardous object 125 may be, for example, a heavy box of merchandise that employees 111 must lift. Hazardous object 125 can also be inherently dangerous, such as a radioactive or chemically toxic object. A few examples of hazardous machinery 113 and equipment 115 include cutting tools, electrical devices, and construction equipment. In addition, workplace environment 109 can be detrimental to the safety of employees 111 if it is prone to fires, breakdowns in proper ventilation, and other lapses in hazard containment.

To monitor the safety of employees 111 as they interact with the workplace, sensors 123 are established in various manners at workplace 109. Sensors 123 can be worn or carried around by employees 111, located on machinery 113, equipment 115, objects 125, and distributed around workplace environment 109. Sensors 123 are configured to take a variety of measurements. For example, motion detectors worn by employees 111 measure body motion as employees 111 move around and carry out various tasks at work.

Multiple motion sensors may be worn on different body parts to obtain detailed body movement information. Motion sensors such as accelerometers and/or gyroscopes may monitor speed, acceleration, position, rotation, and other characteristics of body and appendage motion. There are sensors available for determining the body posture of employees 111, particularly while lifting heavy objects. Chronic and acute back injuries are often the result of lifting objects using an improper lifting behavior, and can lead to high valued workers' compensation claims. Pressure sensors embedded in the footwear of employees 111 or located on the floor of workplace 109 also provide information on the ergonomics of employees 111, such the weight and weight distribution over different parts of the body. Many other types of wearable sensors used to gain information about the work habits of employees 111 can be integrated into safety evaluation system 100, such as chemical sensor and location sensors such as GPS transceivers, assisted GPS sensors and/or magnetometers.

In some embodiments, sensors 123 are used to monitor the movement or activity levels of employees 111 who may not generally work with heavy equipment or machinery. For example, sensors 123 may be used to monitor the movements and/or activity levels of employees 111 such as office workers engaged in desk and/or computer work. These employees may tend to be more sedentary than employees that work with other equipment, machinery, or materials. It has been suggested that daily activity of workers may be directly related to their overall health and wellness. Monitoring the activity levels of workers, especially sedentary workers, provides additional information relevant to evaluating the overall risk of an insurance account to calculate insurance premiums and potential discounts. Sensors that can be used to monitor employee activity levels include physiological sensors such as heart rate sensors, blood pressure sensors, pedometers, or other sensors for sensing physiological signals.

In certain embodiments, the activity levels and/or lifting behavior of injured employees are monitored with sensors 123. Workers in manual material handling jobs who become injured may have limited capabilities during their recovery, at which time they may be able to return to work, but not at full capacity. Sensors 123, which may be worn by an injured employee, may be used by occupational health case workers to monitor the activity level of the injured employee during their recovery in order to facilitate the speed of recovery.

In addition to being worn or carried around by employees 111, sensors 123 are also be fixed on machinery 113, equipment 115, and objects 125. These sensors can also be motion, weight, heat, and pressure sensors, like the wearable sensors discussed above. For example, weight/force sensors may be used to measure the weights of objects 125. Heat sensors provide information on the functionality of machinery 113 and equipment 115. Overheating or malfunctioning equipment/machinery constitute a workplace hazard for employees 111. RFID transponders placed on machinery 113, equipment 115, and objects 125 are used to identify the machinery/equipment/object, or if paired with RFID transponders carried by employees 111, are used to determine the relative location of employees 111 with respect to various pieces of machinery 113, equipment 115, or objects 125.

Sensors 123 that are distributed at fixed locations around workplace 109 include heat sensors that monitor the temperature of the workplace. Digital cameras and camcorders can be mounted around workplace 109 to monitor and analyze employee actions, including lifting behavior when lifting heavy objects. The above described sensors and their purposes are discussed in more detail below in connection with the systems depicted in FIGS. 3 and 4.

Sensors 123 can be configured to transmit data continuously throughout the day, at or during specified periods of time, or in response to the detection of a particular event. Data from sensors 123 are collected and stored on local computer 133. Local computer 133 is a computer, a memory device, or a network of such devices that is capable of collecting, storing, and processing sensor data. Local computer 133 may be a mobile device, such as a smart phone, personal digital assistant (PDA), laptop, or micro PC. Alternatively, local computing device 133 may be an embedded computing platform built into sensors 123. Sensors 123 communicate with local computer 133 via communication system 106. Communications system 106 can be wired or wireless, and can utilize any appropriate protocol, such as Bluetooth®. WiFi, ZigBee, or ANT. The internal communication network 106 between sensors 123 and local computer 133 is part of a larger communications network 127 that allows communication of information between customer 101, insurance company 120, and third party provider 107, whose functions are described further below. The devices connected to communication network 127, and the internal networks contained within, may employ data encryption and security software so that sensitive information, such as the medical histories of employees 111, are protected.

In addition to the data obtained from sensors 123, static data regarding employees 111, such as the age, height, level of physical fitness of each person, and data regarding industry safety standards is stored at an internal database 129 at customer 101. Data in internal database 129 supplements sensor data and is transmitted along with sensor data to insurance company 120 for processing. Internal database 129 may not necessarily be located at customer 101. It can be located or maintained at a remote location, but accessible by customer 101 and/or insurance company 120.

Safety data obtained from sensors 123 and database 129 is transmitted via communications network 127 to insurance company 120 for evaluation. In one implementation, the data is transmitted in raw form directly from the sensors. In another implementation, the data is first processed by local computer 133 and then transmitted to insurance company 120 in synthesized form. The transmitted data may also pass through a third party provider 107. In one scenario, third party provider 107 is an outside expert hired by customer 101 or insurance company 120 to perform the analysis and evaluation of the sensor data. In another scenario, insurance company 120 purchases or obtains in another manner data from third party provider 107 instead of interacting directly with customer 101. Like local database 129, third party provider 107 can also be a source of information on industry safety standards, for example from NIOSH and OSHA.

Insurance company 120 has a computer system 119 that includes application servers 102, load balancing proxy servers 103, data storage unit 104, business logic computer 122, and user interface module 105 to perform risk evaluation and underwriting based on the collected employee safety data. Employees of the insurance company 120 and other authorized personnel use user interface module 105 to access the insurance company computer system. User interface module 105 may be any type of computing device that is configured to communicate with other computer systems. User interface module 105 may be connected directly to application server 102, or may access an application server 102 via the load balancing proxy servers 103. User interface module 105 may connect to load balancing proxy servers 103 via a local area network, a private data link, or via the internet. Although depicted as being part of insurance company 120 in FIG. 1, user interface module 105 may be located remotely, such as onsite at an insured facility. The business logic computer 122 is connected to the data storage unit 104 and application servers 102 over a local area network 121, which may be part of communication system 127. In addition, other network infrastructure, including, for example a firewall, backup servers, and back up data stores, may also be included in the system 119, without departing from the scope of the invention. Communications over the local area network 121 and/or over the Internet, in one implementation, are encrypted. In addition, such communications, whether encrypted or not, may also be digitally signed for authenticating the source of the communications. The computer system 119 may also include a certificate authority to authenticate one or more of the communications using public key infrastructure.

Based on employee safety data collected from the various sources described above, a safety evaluation module analyzes and evaluates employee safety of customer 101. As used herein, a "module" is a processor or portion of a processor configured to perform one or more functions. In some embodiments, the module includes hardware and software executing on the hardware for performing particular functions. Optionally, the module includes hardware specifically designed to perform particular functions, or includes hardware and firmware specifically configured to perform particular functions. In some embodiments, a module includes executable code that, for instance, comprise one or more physical or logical blocks of computer instructions which may, for instance, be organized as an object, procedure, or function. Nevertheless, the executables in a module need not be physically located together, but may comprise disparate instructions stored in different locations which, when joined logically together, comprise the software portion of the module and achieve, along with hardware, the stated purpose for the module.

Indeed, a module of executable code could include a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. In addition, entire modules, or portions thereof, may also be implemented in programmable hardware devices such as field programmable gate arrays, programmable array logic, programmable logic devices or the like or as hardwired integrated circuits.

In one implementation, the safety evaluation module is implemented in business logic computer 122. In other implementations, the safety evaluation module is implemented in application servers 102, on local computer 133, or is distributed across multiple elements of system 119. After the safety evaluation module evaluates the safety condition of customer 101, it sends feedback back to customer 101 via communications network 127 that is directed towards improving employee workplace safety. Feedback is provided to employees 111 through a visual, audio, or tactile stimulus, which is represented by flashing lights 130 in FIG. 1. Flashing lights 130 may, for example, flash when an employee 111 enters into a hazardous area or adopts an unsafe posture when lifting heavy object 125. Other types of feedback mechanisms include a vibrating device worn by employee 111 or an audio buzzer. Feedback may also be given to a manager, and then relayed to employee 111 in an indirect manner, such as in a verbal conversation between the manager and employee 111.

A business logic module, implemented preferably in business logic computer 122, is used to underwrite or alter workers' compensation insurance pricing for customer 101 based on the received data. The business logic module may use predictive models, such as neural networks, Bayesian networks, and support vector machines, in performing the underwriting and premium adjustment. In one embodiment, the premium of the insurance policy is decreased if customer 101 employees exhibit safe practices. Conversely, insurance premiums are increased in response to unsafe employee performance. Instead of altering premium rates, other terms of the insurance policy can be altered, such as the policy deductible.

In another scenario, insurance company 120 awards customer 101 with premium discounts, or other advantageous rewards, simply for instituting a safety evaluation and feedback system. In this scenario, insurance company 120 does not receive actual safety data from customer 101. Insurance company 120 may award different discounts depending on policies instituted by customer 101 based on the output of the safety evaluation and feedback system. For example, insurance company 120 may award a discount if customer 101 has a safety policy of giving salary bonuses to employees 111 with good safety records. Insurance company 120 may also award a discount if customer 101 has a reward policy that promotes active participation of employees 111 in the safety evaluation system. These scenarios are described in more detail further below in connection with FIGS. 3 and 4.

Figure 2:
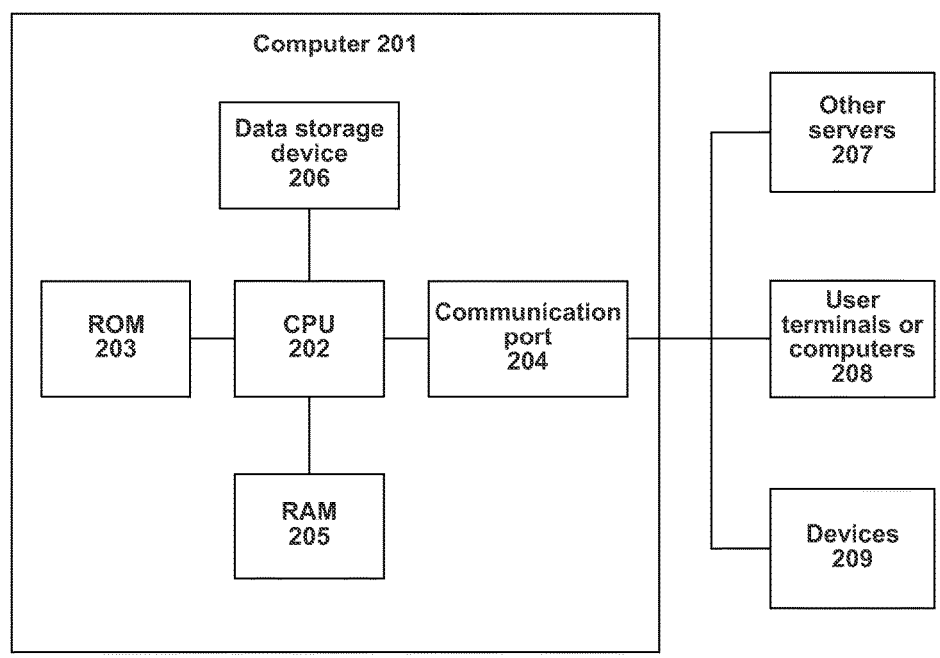
FIG. 2 is a block diagram of a computer network system that may be used in an embodiment of the invention.

Business logic computer 122 may be implemented based on the computer network system architecture shown in FIG. 2. Business logic computer 122 may have data storage capabilities of its own, or may access external data storage unit 104 for such purposes. In one implementation, data storage unit 104 is a data warehouse utilized by the insurance company 120. The data warehouse is the main electronic depository of the insurance company's current and historical data. The data warehouse includes one or more interrelated databases that store information relevant to insurance data analysis. The interrelated databases store both structured and unstructured data. In one implementation, one or more of the interrelated databases store electronic copies of insurance forms, either in an image format or a text-searchable format keyed to a customer or claim. Other databases in the interrelated databases store data, for example, in a relational database, in various data fields keyed to various identifiers, such as, without limitation, customer, data source, geography, or business identifier (such as Standard Industry Classification Code). The information stored in the data warehouse 104 is obtained through communications with customers, agents, vendors, sensors, and third party data providers and investigators. In particular, the data warehouse is configured to store data about customer employee safety, as well as related loss information, if any. Preferably, the computations required for risk evaluation and underwriting are primarily carried out by business logic computer 122, in order to free up the other resources for other tasks. The processes performed by business logic computer 122 in illustrative embodiments of the invention are described below in relation to FIGS. 3 and 4.

In one implementation, software operating on the application servers 102 act merely as presentation and data extraction and conversion servers. All substantive business logic, including underwriting and pricing determinations, is carried out on the business logic computer 122. In this implementation, the application servers 102 obtain data from the data storage unit 104 and the business logic computer 122 and incorporate that data into web pages (or other graphical user interface formats). These web pages are then communicated by the application servers 102 through the load balancing proxy servers 103 to user interface module 105 for presentation. Upon receiving input from user interface module 105, the application server 102 translates the input into a form suitable for processing by the business logic computer 122 and for storage by the data storage unit 104. In this implementation, the application servers can be operated by third parties, who can add their own branding to the web pages or add other customized presentation data. In the alternative, at least some of the business logic is also carried out by the application servers 102. Application servers 102 may also include a webserver for automatically recovering or retrieving safety data from local computer 133.

In another implementation, the application servers 102 are software modules operating on one or more computers. One of the computers on which the application servers 102 are operating may also serve as the business logic computer 122 and/or as a load balancing proxy server 103.

In other implementations, the software operating on user interface module 105 includes a thin or thick client application in addition to, or instead of web browser. The thin or thick client application interfaces with a corresponding server application operating on the application server 102.

FIG. 2 is a block diagram of a computing architecture suitable for implementing various ones of the computing devices depicted in FIG. 1, including, for example, the business logic computer 122, application servers 102, and user interface module 105.

Computer 201 comprises at least one central processing unit (CPU) 202, at least one read-only memory (ROM) 203, at least one communication port or hub 204, at least one random access memory (RAM) 205, and one or more databases or data storage devices 206. All of these later elements are in communication with the CPU 202 to facilitate the operation of the computer 201. The computer 201 may be configured in many different ways. For example, computer 201 may be a conventional standalone computer or alternatively, the function of computer 201 may be distributed across multiple computing systems and architectures.

Computer 201 may be configured in a distributed architecture, wherein databases and processors are housed in separate units or locations. Some such units perform primary processing functions and contain at a minimum, a general controller or a processor 202, a ROM 203, and a RAM 205. In such an embodiment, each of these units is attached to a communications hub or port 204 that serves as a primary communication link with other servers 207, client or user computers 208 and other related devices 209. The communications hub or port 204 may have minimal processing capability itself, serving primarily as a communications router. A variety of communications protocols may be part of the system, including but not limited to: Ethernet, SAP, SAS™, ATP, BLUETOOTH™, GSM, ZipBee, ANT, and TCP/IP.

The CPU 202 comprises a processor, such as one or more conventional microprocessors and one or more supplementary co-processors such as math co-processors. The CPU 202 is in communication with the communication port 204 through which the CPU 202 communicates with other devices such as other servers 207, user terminals 208, or devices 209. The communication port 204 may include multiple communication channels for simultaneous communication with, for example, other processors, servers or client terminals. Devices in communication with each other need not be continually transmitting to each other. On the contrary, such devices need only transmit to each other as necessary, may actually refrain from exchanging data most of the time, and may require several steps to be performed to establish a communication link between the devices.

The CPU 202 is also in communication with the data storage device 206. The data storage device 206 comprises an appropriate combination of magnetic, optical and/or semiconductor memory, and may include, for example, RAM, ROM, flash drive, an optical disc such as a compact disc and/or a hard disk or drive. The CPU 202 and the data storage device 206 each may be, for example, located entirely within a single computer or other computing device; or connected to each other by a communication medium, such as a USB port, serial port cable, a coaxial cable, a Ethernet type cable, a telephone line, a radio frequency transceiver or other similar wireless or wired medium or combination of the foregoing. For example, the CPU 202 may be connected to the data storage device 206 via the communication port 204.

The data storage device 206 may store, for example, (i) a program (e.g., computer program code and/or a computer program product) adapted to direct the CPU 202 in accordance with the present invention, and particularly in accordance with the processes described in detail hereinafter with regard to the CPU 202; (ii) databases adapted to store information that are utilized to store information required by the program. Suitable databases include data storage unit 104 of FIG. 1.

The program may be stored, for example, in a compressed, an uncompiled and/or an encrypted format, and include computer program code. The instructions of the program may be read into a main memory of the processor from a computer-readable medium other than the data storage device 206, such as from a ROM 203 or from a RAM 205. While execution of sequences of instructions in the program causes the processor 202 to perform the process steps described herein, hard-wired circuitry may be used in place of, or in combination with, software instructions for implementation of the processes of the present invention. Thus, embodiments of the present invention are not limited to any specific combination of hardware and software.

Suitable computer program code may be provided for performing numerous functions such as safety data processing and insurance policy underwriting. The program also may include program elements such as an operating system, a database management system and "device drivers" that allow the processor to interface with computer peripheral devices 209 (e.g., a video display, a keyboard, a computer mouse, etc.).

The term "computer-readable medium" as used herein refers to any medium that provides or participates in providing instructions to the processor of the computing device (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM or EEPROM (electronically erasable programmable read-only memory), a FLASH-EEPROM, any other memory chip or cartridge, or any other medium from which a computer can read.

Various forms of computer readable media may be involved in carrying one or more sequences of one or more instructions to the processor 202 (or any other processor of a device described herein) for execution. For example, the instructions may initially be borne on a magnetic disk of a remote computer 208. The remote computer 208 can load the instructions into its dynamic memory and send the instructions over an Ethernet connection, cable line, or even telephone line using a modem. A communications device 204 local to a computing device (or, e.g., a server) can receive the data on the respective communications line and place the data on a system bus for the processor. The system bus carries the data to main memory, from which the processor retrieves and executes the instructions. Optionally, the instructions received by main memory are stored in memory either before or after execution by the processor. In addition, instructions may be received via a communication port as electrical, electromagnetic or optical signals, which are exemplary forms of wireless communications or data streams that carry various types of information.

As previously discussed with reference to FIG. 1, servers may also interact and/or control one or more user devices 209, such as displays and printers, or remote computers 208 such as, e.g., user interface module 105. User device 209 may include any one or a combination of a personal computer, a laptop, a personal digital assistant, a mouse, a keyboard, a computer display, a touch screen, LCD, voice recognition software, or other generally represented by input/output devices required to implement the above functionality.

Figure 3:
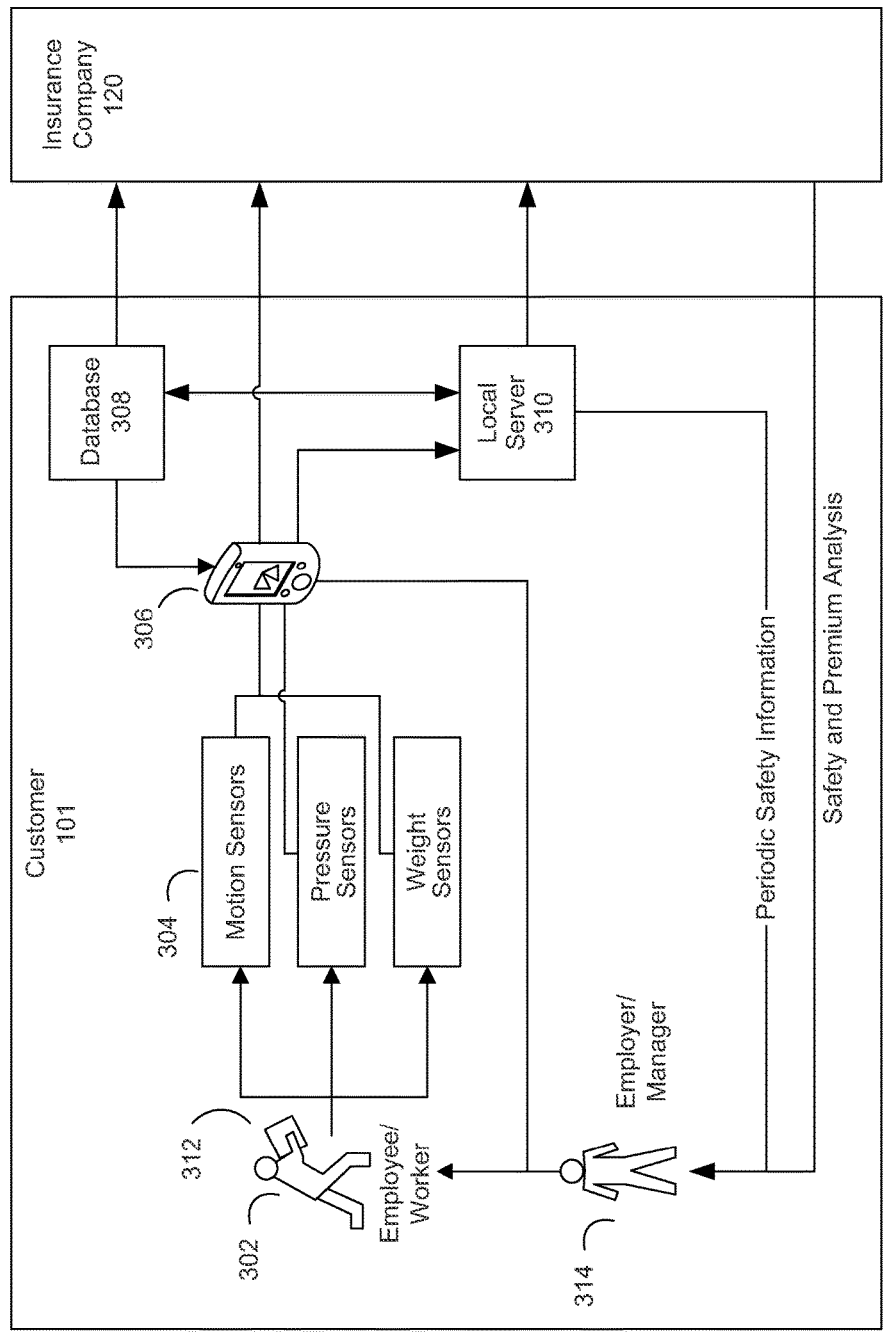
FIG. 3 is a schematic diagram of a first employee safety evaluation system, according to an illustrative embodiment of the invention.

FIG. 3 is a schematic diagram of an illustrative employee safety monitoring and evaluation system where customer 101 is insured by insurance company 120. In FIG. 3, employee 302 of customer 101 is lifting a heavy object 312. This system is configured to monitor the likelihood of stress and strain injuries, which constitute a large potion of workers' compensation claims. As a participant of a safety evaluation system, employee 302 wears sensors 304 on his body to monitor his body posture, movement, and other lifting behavior while lifting object 312. Sensors 304 may be, for example, footwear with embedded weight/force sensors that measure his weight distribution, heat sensors to monitor overheating or overexertion, and digital cameras to capture lifting behavior information.

As employee 302 performs the task of lifting object 312, the above described sensors transmit data to computing device 306. In one embodiment, computing device 306 is a mobile computing device, such as a smart phone, laptop, micro PC, or an embedded computing platform built into the sensor platform. Data is transferred between sensors 304 and computing device 306 via any kind of wireless communication system, such as a Bluetooth® or WiFi network. Computing device 306 collects, aggregates, and stores the transmitted data. Computing device 306 also performs calculations and analyses on the transmitted data, such as noise filtering and mathematical operations to synthesize more meaningful data.

In addition to data derived from sensors, static data is also available and stored in database 308. Static data includes data such as the name, medical history, job characteristics, and other personal facts regarding employee 302. Static data also includes the weight, attachment points, and dimensions of object 312. This type of data is used by computing device 306 in conjunction with sensor data to evaluate the safety of employee actions. For example, it could be considered unsafe for an employee weighing 110 lbs and in poor physical shape to lift a 50 lbs object, while a different employee weighing 150 lbs and in good shape could do the same task safely. Static data stored in database 308 optionally includes industry safety standards set by NIOSH and OSHA. These industry standards are used in some implementations as a benchmark for safety evaluation. In some embodiments, the safety evaluation results in a lifting safety indicator that insurance company 120 uses in altering the policy terms.

Computing device 306 provides employee 302 with immediate feedback about his lifting behavior through a stimulus. For example, a light may blink whenever employee 302 adopts unsafe lifting behavior. Alternatively, a vibrating apparatus worn by employee 302 or an audio stimulus is activated to relay the same message. In one implementation, feedback stimuli is activated by computing device 306 only when employee actions pass a certain quantitative threshold. To obtain a safety evaluation score to compare to the threshold, computing device 306 applies a quantitative algorithm to the received data.

In addition to computing device 306, which may be a handheld mobile device and insufficient for all the computing and storage needs of the evaluation system, there may be a local server 310 connected to computing device 306. Local server 310 communicates directly with database 308 and sensors 304. Data may be transferred between local server 310 and the other elements of the system via a USB, wired LAN, WiFi, or cellular connection. The network connection is preferentially secure so that personal data such as employee medical history is protected. Local server 310 performs local processing such as collecting raw sensor data over time and aggregating information for analysis across all users of the safety evaluation system. Local server 310 can be located onsite at customer 101 or be a product or service offered by a third party.

In one implementation, local server 310 generates periodic safety reports on all the employees 302 for management of customer 101. Management can then use these reports to provide feedback to employees 302 to promote safer behavior. These reports may also be used by management to create policies that promote safe behavior. For example, the fraction of safe to unsafe lifts performed by an employee 302 or other lifting safety indicators can be included in the report, and management may award employee 302 a year-end bonus or other benefit or recognition based on this indicator.

In some embodiments, local server 310, computing device 306, database 308, and sensors 304 also transmit data directly to insurance company 120. Data transmission between these elements and insurance company 120 may occur in a variety of ways, such as via secure email, HTTPS protocol, and XML messages over a SOAP protocol. Insurance company 120 may use this data for safety and premium analysis.

Safety analysis includes any safety assessment, risk evaluation, or risk improvement services. Services offered may include loss control services such as the dispatch of safety experts employed by insurance company 120 to advise on dangerous scenarios at the workplace. Loss control services may be provided, for example, after insurance company 120 is alerted of unsafe circumstances at a customer workplace through reports sent from local server 310. Modification of these services based on the received data may include an increase or decrease in frequency of the service, a change in the cost of the service, and targeting a specific safety concern.

Premium analysis includes activities that potentially affect a customer's premium, deductible amount, discounts or credits, as well as large scale analysis to provide input into industry or occupation experience factors. The determination of premium and offering of discounts or credits may be performed once at underwriting time, regularly on an interval, continuously, in response to an event, or retroactively, as permitted by local, state, and/or federal regulations.

The analysis and decisions made by insurance company 120 with regard to premium/service adjustments and safety evaluation may be transmitted back to customer 101. This information may be stored at local server 310, or on another device at customer 101. This information may be directly accessible by employees 302 of customer 101 or may be relayed to employees 302 by manager 314.

Insurance company 120 may save the data and reports received from customer 101, and the decisions that were made based upon them, in data storage unit 104, which was discussed in FIG. 1, or in a separate data warehouse. This archived data may be used for future retrospective analysis, claims adjudication, and/or to support fraud investigation.

Figure 4:
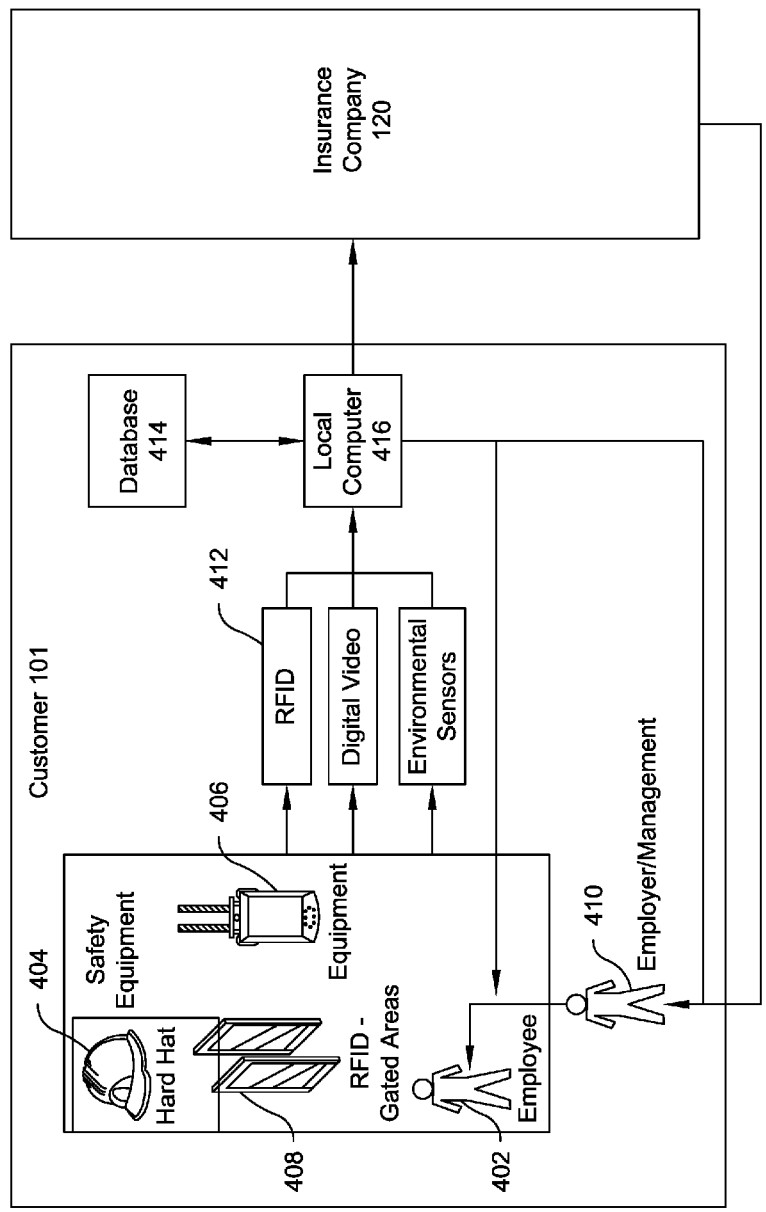
FIG. 4 is a schematic diagram of a second employee safety evaluation system, according to an illustrative embodiment of the invention.

Another illustrative employee safety monitoring and evaluation system is shown in FIG. 4. Other major sources of peril in the workplace include lack of compliance with best practices for use of personal protective equipment and other guidelines regarding off-limits hazardous areas and permission to use dangerous equipment. For example, it is well understood that safety goggles should be used when operating certain machinery, such as a lathe. The system shown in FIG. 4 may be used to monitor and promote compliance with such guidelines, and appropriately alter insurance policy terms in response to changes in compliance.

Like in FIG. 3, customer 101 employing employees 402, is insured by insurance company 120. Employee 402 may perform a job that requires protective clothing or equipment 404, such as hard hats, goggles, gloves, boots, and lifting belts. For example, employee 402 may be a lathe operator. While it is in the employee's best interest to wear protective clothing 404 and customer 101 may have policies requiring protective clothing, employee 402 may intentionally or unintentionally fail to comply with these policies. A safety monitoring system can promote compliance and lead to fewer injuries at the workplace.

In the system depicted in FIG. 4, articles of personal protective equipment 404 are tagged with inexpensive RFID chips. The hazardous equipment 406 that employee 402 operates is equipped with sensors, such as an RFID reader for detecting the presence of personal protective equipment. Examples of hazardous equipment include hand tools, power tools, machine tools, construction equipment and vehicles, and chemically toxic and physically fragile objects. A motion detector, such as an infrared motion sensor, may also be located on or near equipment 406. The motion detector may have a range of less than a few meters, so that it senses only motion very close to it. When employee 402 approaches equipment 406, the motion detector is activated, triggering the RFID reader. The RFID reader detects the RFID tagged personal protective equipment 404, or lack thereof, and recognizes the employee 402. Employee identity information may be stored in the RFID chip if the protective clothing is not shared. Otherwise, a separate RFID chip may be embedded in employee 402's ID card or in another convenient object.

In one implementation, equipment 406 is configured to stay inactive unless RFID tagged personal protective equipment is detected. Thus, employee 402 cannot operate equipment 406 without wearing appropriate personal protective equipment 404. In another implementation, an employee's presence in the vicinity of equipment 406 without personal protective equipment 404 may trigger an alarm. For example, if an employee activates the motion detector, but the RFID scanner does not detect a corresponding chip, then an alarm will sound to alert the employee that he is not wearing personal protective equipment 404. The alarm may also be concurrently transmitted to employee 402's supervisor and medical personnel in some situations, such as when employee 402 approaches chemically toxic or radioactive equipment 406 without a radiation suit.

The system can log the number of times employee 402 attempts to handle or operate equipment 406 without proper personal protective equipment 404. This information can be used by insurance company 120 to evaluate the safety of employee 402's behavior. The results of the evaluation can be used by insurance company 120 to alter the terms of the insurance policy.

Although the system above is described as being implemented using RFID technology, other types of technology may also be used to accomplish the same goals. One example is digital photography and image analysis, which can be used to identify employee 402 and personal protective equipment 404. GPS, assisted GPS, floor pressure sensors, and motion detectors are other technologies that can be utilized, alone or in combination, to implement the above described safety monitoring and alert system. In addition, sensors can be combined into sensor networks and incorporated into the system.

Another scenario where the above described monitoring and alert system may be utilized is in monitoring employee 402 activity and presence in hazardous areas at a workplace. Hazardous area 408 may be the vicinity around high voltage electrical equipment, radioactive or chemically toxic areas, areas with dangerous moving parts such as engine rooms, and other places with high likelihood of accidents. In general, customer 101 may want to dissuade employees 402 from entering hazardous areas 408 unless they have a reason to be there and are trained in any special skills that may be necessary.

One method for monitoring activity in hazardous areas 408 is to establish RFID tagged gates 412 around the areas. In this manner, only employees 402 granted with access may enter such areas. In some cases, it might not be desirable to institute such strict requirements around some hazardous areas 408. For example, customer 101 may want to dissuade employees 402 from entering a moderately dangerous work zone, but does not want to implement a more complex system to prevent it. In this case, RFID scanners located at the work zone identify and keep track of the number of times employee 402 enters the zone, but do not actively prevent it. However, by logging the number of times employee 402 enters the zone, feedback can be given to that employee to promote safer behavior in the future. For example, employee 402's manager may have access to the logs and may notify employee 402 verbally.

Other sensors can also be used in addition to, or in place of, RFID tags to implement the system described above. For example, GPS systems can be used to track employee locations and digital photography and photo recognition systems can be used for personnel identification.

Hazardous areas 408 may be equipped with environmental sensors that monitor heat, carbon monoxide, carbon dioxide, and smoke levels. These sensors may be linked to alarms so that immediate feedback and evacuation can be facilitated.

Similar to the embodiment described in FIG. 3, data from sensors located on employees 402, personal protective equipment 404, hazardous equipment 406, and hazardous areas 408 may be transmitted to a local computer 416 for collection, aggregation, and processing. The data may be transmitted via any appropriate wired or wireless, secure or open, communications protocol, as discussed previously in FIG. 3. Local computer 416 may process the sensor data to obtain useful information, such as image analysis on digital camera footage. Local computer 416 may also receive input from database 414, which stores static data regarding the employees 402, personal protective equipment 404, hazardous equipment 406, and hazardous areas 408, such as employee identity, employee access rights to certain areas, employee training level for certain tasks and equipment, and safety information on hazardous equipment 406 owned by customer 101. Local computer 416 may be operated by customer 101 or may be a service/product that is offered by a third party.

Based on the collected sensor data and static information from database 414, local computer 416 may determine the number of times a particular employee 402 fails to comply with safety standards, and generate an a safety evaluation of customer 101's workplace. Local computer 416 may also aggregate safety data across all employees and generate reports for management 410.

Raw data from sensors 404 and processed data from local computer 416 may be transmitted to insurance company 120. Insurance company 120 may perform safety analysis and premium analysis on the data, as discussed above in connection with FIG. 3.

The analysis and decisions made by insurance company 120 with regard to premium/service adjustments and safety evaluation may be transmitted back to customer 101. This information can be stored at local computer 416, or on another device at customer 101. This information may be directly accessible by employees 402 of customer 101 or may be relayed to employees 402 by manager 410.

Insurance company 120 may save the data and reports received from customer 101, and the decisions that were made based upon them, in data storage unit 104, which was discussed in FIG. 1, or in a separate data warehouse. This archived data may be used for future retrospective analysis, claims adjudication, and/or to support fraud investigation.

The embodiments depicted in FIGS. 3 and 4 illustrate exemplary implementations of a safety monitoring and evaluation system. These implementations can also be used in combination to concurrently monitor physical actions performed by employees, personal protective equipment use, and other safety-related behaviors.

Figure 5:
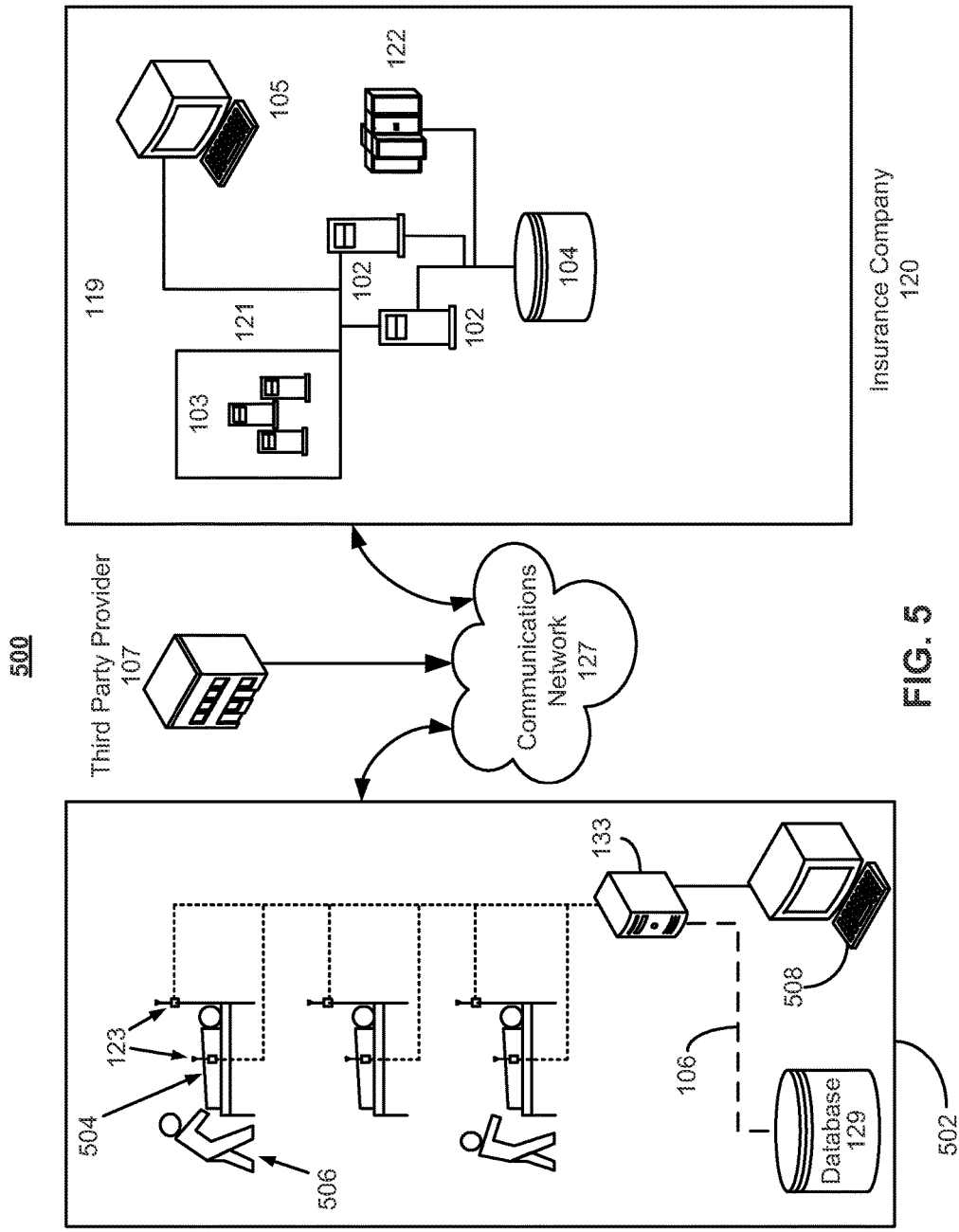
FIG. 5 is a schematic diagram of a patient monitoring and evaluation system, according to an illustrative embodiment of the invention.

FIG. 5 is a schematic diagram of an illustrative patient monitoring and evaluation system 500, according to one embodiment of the invention. System 500 is similar to system 100 described in FIG. 1, with many of the elements described in system 100, except that system 500 is directed to a healthcare facility 502, such as a hospital, nursing home, assisted-living facility, long or short-term rehabilitation hospital, or other facility providing health care. The insurance company 120 in FIG. 5 provides insurance to the healthcare facility 502 and/or to a patient 504 receiving treatment in the healthcare facility 502. The patient 504 wears sensors 123 for monitoring his or her body movements and activity. For example, the patient 504 may wear sensors 123 around his or her waist. In some embodiments, other sensors not worn by the patient may also be disposed to monitor patient movements and activity. For example, video cameras or motion detectors may be mounted within the patient's room, or upon the patient's bed. Sensor data is collected upon the detection of movement or activity, and may be compiled periodically to provide a movement/activity score or level. For example, sensor data may be compiled in a particular time interval, such as eight hours, to compute a movement score for that time interval.

In certain embodiments, the system 500 may be used to monitor a patient's recovery or rehabilitation progress. For example, the monitored movement/activity metrics of the patient 504 can be used to determine whether the patient 504 is recovering at a sufficient pace, or whether additional care should be provided. For example, if patient 504 suffered from a broken limb, the movement/activity metrics of the patient 504, including movement of his entire body and/or the affected limb, may be used to determine if the limb is moving too much, not enough, and/or whether the patient 504 is performing prescribed rehabilitation exercises at the appropriate times. In some embodiments, the monitored movement/activity metrics of the patient 504 is compared to an expected rehabilitation timeline or schedule. If the monitored metrics do not meet the timeline or schedule, additional care or treatment may be provided to the patient 504.

In some embodiments, where patient 504 is bedridden or otherwise motion-restricted, the monitored movement/activity metrics of the patient 504 are used to determine if he or she is being moved, shifted, or turned sufficiently often to prevent conditions such as decubitus ulcers. Physicians may prescribe that a patient be "turned" in bed at set intervals. Typical guidelines hold that prevention of such ulcers consists of changing the patient's position every two hours or more frequently if the patient's conditions requires. This two-hour time frame is a generally accepted maximum interval that the tissue can tolerate pressure without damage. Patients confined to bed for extended periods of time may require more frequent attention. It is often difficult to know if a patient has been moved as prescribed. The monitored movement/activity metrics allow provide feedback, reminders, and/or prompts to staff to move patients at prescribed intervals.

In some embodiments, the system 500 includes a user terminal 508 configured to allow health care staff and/or third-party monitoring personnel such as case workers to input prescribed motion and/or activity guidelines, such as how often patient 504 should be turned or moved, how much patient 504 should be turned or moved, and/or movement thresholds beyond which health care personnel are to be notified. User terminal 508 may also be configured to allow personnel to monitor the movement/activity of patient 504 and whether health care staff are following the prescribed motion/activity guidelines, and/or to provide reports or summaries of the movement/activity history for patient 504. In certain embodiments, monitoring the movement/activity metrics of a patient that is particularly weak and unable to move independently may prevent asphyxiation, which may occur if the patient accidentally turns over so as to lie face-down. In this situation, the system 500 is configured to notify health care staff via, for example, user terminal 508 if movement/activity is detected. In some embodiments, user terminal 508 may be a nurses' station and is also communicatively coupled with other devices via the network 127, such as computer system 119, database 129, and/or other nurses' stations at the facility.

Figure 6:
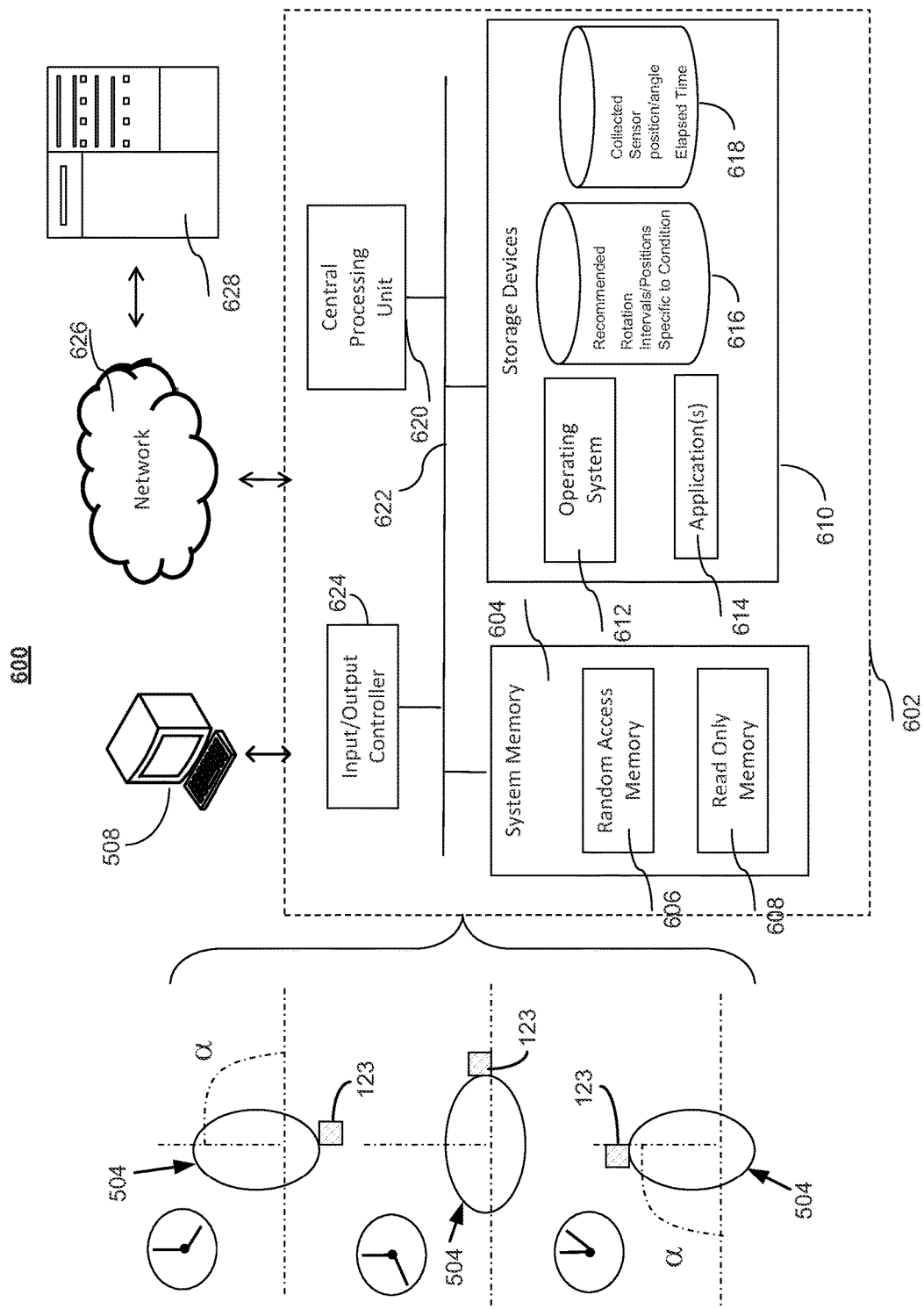
FIG. 6 is a schematic diagram of a patient monitoring system for determining movement of bedridden patients, according to an illustrative embodiment of the invention.

FIG. 6 is a schematic diagram of a patient monitoring system 600 for determining movement of bedridden patients, according to an illustrative embodiment of the invention. Wearable sensor(s) 123 is attached to or worn by bedridden patient 504. The wearable sensor(s) 123 are configured to detect the patient 504's direction of movement, extent of movement, as well as the patient's degree of rotation. As discussed above, certain movement thresholds are prescribed for bedridden patients in order to prevent ailments such as decubitus ulcers. These movement thresholds include the time between movement, extent of movement, and allowable positions. For example, the prescribed movement thresholds for a patient may state that he should be moved every two hours, that every time he is turned, he should be turned approximately 90 degrees axially so that he lies on a different portion of his body (e.g., his left side, his right side, his back), and that he should not lie on the same portion of his body more than once every six hours (e.g., he should be turned such that he lies on every portion at least once every six hours). An embodiment of this is shown in FIG. 6, where the body cross-section of the patient 504 is shown, along with the attached/worn sensor(s) 123, at various times within a particular time period.

The sensor(s) 123 are communicatively coupled to a computer 602, similar to local computer 133 and computer 201, described above in relation to FIGS. 1 and 2. The computer 602 includes system memory 604, which includes random access memory 606 (similar to RAM 205, FIG. 2) and read only memory 608 (similar to ROM 203, FIG. 2). The computer 602 also includes a central processing unit 620 similar to CPU 202 (FIG. 2), storage devices 610 similar to data storage device 206 (FIG. 2), and an input/output controller 624. Similar to data storage device 206 (FIG. 2), storage devices 610 stores an operating system 612 and application(s) 614. Storage devices 610 also stores database 616 containing prescribed or recommended movement thresholds for patients, as well as database 618 containing position and angle data collected by the sensors 123, as well as elapsed time data. The input/output controller 624, with which CPU 620 communicates, allows the CPU 620 to communicate with other devices such as other servers, user terminals, or devices. The input/output controller 624 may include multiple communication channels for simultaneous communication with, for example, other processors, servers or client terminals. Devices in communication with each other need not be continually transmitting to each other. On the contrary, such devices need only transmit to each other as necessary, may actually refrain from exchanging data most of the time, and may require several steps to be performed to establish a communication link between the devices. Interconnect bus 622 facilitates communication between the various components of the computer 602.

The system 600 includes a user terminal 508 communicatively coupled with computer 602, similar to user terminal 508 described in FIG. 5. The computer 602 is also communicatively coupled with computer system 628, similar to computer system 119 (FIG. 1), via network 626, similar to communications network 127 (FIG. 1).

Since sensors 123 may be configured to monitor the movement/activity of a particular person wearing the sensors, in some embodiments the sensors 123 are equipped to detect if they are removed from the person. By detecting the removal of the sensors 123, the accuracy of the monitored movement/activity data can be determined, any anomalous activity can be detected, and appropriate actions can be taken. For example, if sensors 123 worn by a recovering injured employee or a bedridden patient are removed at some point during the day, the movement/activity data measured by the sensors 123 after the removal will not reflect the actual activity or movement of the injured employee or the patient. Besides the problem associated with collecting inaccurate data, this can be particularly problematic, because relevant personnel may not be notified if, for example, an injured employee unknowingly tries to lift beyond his prescribed thresholds, or if a patient is not turned and moved at the prescribed times. Thus, the sensors 123 may be configured to detect its removal from the relevant person, and to notify appropriate monitoring personnel and/or to log the removal in local or remote memory.

FIGS. 7A-D depict various views of a wearable sensor 700, similar to worn sensors 123 described in FIGS. 1 and 5, according to an illustrative embodiment of the invention. Wearable sensor 700 is configured to detect its removal from a person wearing it. Wearable sensor 700 includes a sensor body or housing 702 attached to a mechanical fastener. The mechanical fastener includes clip arm 704 and hinge 706, which attaches the clip arm 704 to the sensor body/housing 702. The clip arm 704, hinge 706, and sensor body/housing 702 are configured to fasten the wearable sensor 700 to a belt or some other article of clothing worn by a monitored individual. FIG. 7A depicts a side view of the wearable sensor 700 when the mechanical fastener is in a closed, fastened position. In the fastened position, electrical contacts 708 form an electrical short, detectable via detection circuitry embedded within the sensor body/housing 702 and/or within the clip arm 704. For the sensor 700 to be removed from a monitored individual, it will be necessary to open the mechanical fastener. When the mechanical fastener is opened, it will assume the configuration shown in FIG. 7B, where the electrical contacts 708 no longer form an electrical short, and instead form an electrical open circuit. The detection circuit detects this open circuit, and can take appropriate action, such as warning the monitored individual, logging the time at which the break in the circuit occurred, and/or notifying monitoring personnel that a circuit break has occurred. FIGS. 7C-D show back views of the wearable sensor 700, showing the sensor body/housing 702, the clip arm 704, the hinge 706, and the electrical contacts 708.

In some embodiments, the electrical contacts 708 may be located within the hinge 706, or elsewhere between the clip arm 704 and the sensor body 702, as long as it is able to detect a change in the position of the clip arm 704 and the sensor body 702 indicative of a release of the fastening mechanism. In certain embodiments, other contact detection and/or mechanical methods may be used, in addition to or in place of the body/hinge/arm fastener and electrical contacts 708. For example, physical connectors such as bands, tapes, or strips may be used to fasten the wearable sensor 700 to an individual. These physical connectors can be configured to detect ruptures in the connectors, for example via embedded conductive wires. Optionally, magnetic sensors may be used to detect if sensor 700 is removed, for example by detecting changes in magnetic field.

Figure 8:
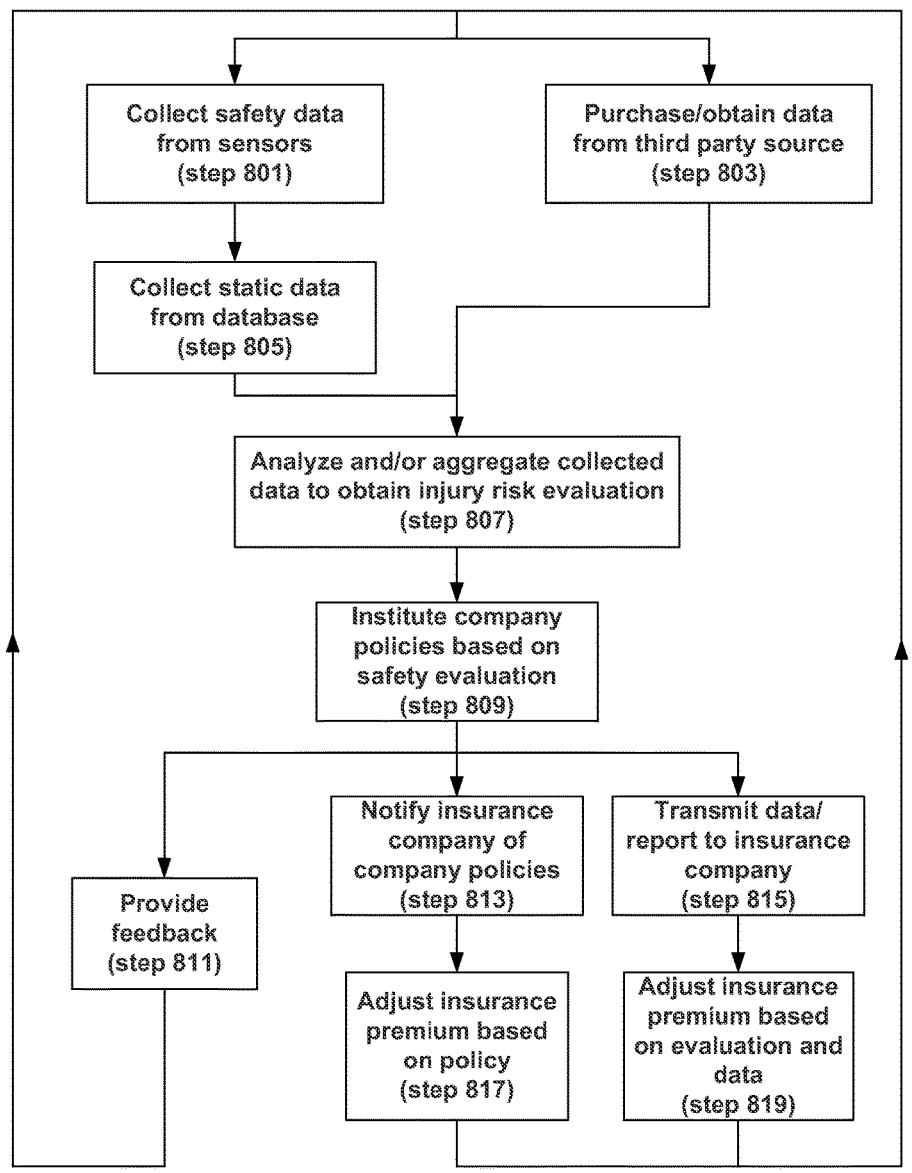
FIG. 8 is a flowchart of a method for evaluating employee workplace safety, according to an illustrative embodiment of the invention.

FIG. 8 is a flow chart of exemplary steps in a method for evaluating and improving workplace safety. The method begins with collecting data from sensors located at the workplace of an insured customer (step 801). The sensor data is related to employee safety. As previously described, sensors at the workplace measure environmental factors such as temperature, carbon monoxide, carbon dioxide, smoke, pressure, and another factors that may affect the safety of the workplace. Sensors may also be worn by employees to collect information on employee actions. Such sensors may include pressure sensors embedded in shoes, and measure lifting behavior and weight distribution of the wearer while he performs certain acts on the job, such as lifting heavy objects. Employee actions such as running, throwing, reaching, falling, and material handling can also be measured. Other types of sensors include digital cameras, weight/forces pads on the ground, infrared motion sensors, and RFID transponders on equipment, protective clothing, and employee identification cards.

Systems in which these sensors are used are described above in connection with FIGS. 3 and 4.

The sensor data may be collected by mobile computing devices, such as laptops, smart phones, and PDAs, and data may be transmitted via a wireless communication protocol, such as Bluetooth® or WiFi. Sensor data may also be collected on a local computer or server.

In addition to sensor data, static data is collected at step 805. Static data may include personal information on employees, such as their medical history, level of physical fitness, job description, level of restricted access, and their current safety evaluation. Static data may also include data on objects and equipment at the workplace, such as the ergonomics (size, shape, dimensions, weight) of objects that are handled by employees, operation procedures of certain equipment, and the degree of hazard of certain work zones. In general, static data encompasses any relevant data that is not being collected in real time from sensors, including industry standards from NIOSH and OSHA. Static data may be stored at a local server.

In addition to or instead of collecting data from sensors and local static data servers, data may also be purchased or obtained from a third party (step 803). The purchased data may be used to supplement the sensor data or may be used to validate or debug the system. The purchased data may include sensor data as well as static data.

Whether the safety data is derived from sensors, a static database, or from a third party, it is analyzed, processed, and aggregated at step 807. Data may be aggregated over all the employees or it may be aggregated over a particular time interval. In some embodiments, the aggregated data are generated into reports, which can then be provided to interested parties (see step 811 below).

Data processing includes applying algorithms to the collected data, which may be in its raw form, to obtain values of interest. For example, raw sensor data may be noise filtered.

In some embodiments, the raw sensor data, processed data, and static data are combined at this step and analyzed to obtain a safety evaluation of the workplace. The evaluation may be a score or a qualitative description. The evaluation may be compared to NIOSH and OSHA safety standards to obtain a pass/fail or a good/bad characterization.

Using the safety evaluation, the insured company may institute policies to promote safe practices at step 809. For example, the insured company may offer bonuses to employees who obtain a good safety evaluation or who are willing to participate in the evaluation program. The insured company may also hold training programs to teach remedial safety practices, such as proper lifting techniques, to those determined by the evaluation system to exhibit unsafe practices. Other policies instituted by the insured company include employer recognition programs that publicly recognize employees identified by the system as safe employees, and stricter suspension or other punitive policies for employees who do not comply with the safety rules as determined by the system.

In response to insured company instituting the above mentioned policies, or other policies designed to promote a safe working environment, the insurance company can favorably alter the terms of the insurance policy, such as decreasing the premium or deductible.

At step 811, safety evaluations, in the form of reports for the entire company, individual customer facilities, employee teams, or individual employees may be provided to the company or individual as feedback. For example, a manager may receive a report indicating that a particular employee was not compliant with safety rules a certain percentage of time. The manager may relay that information to the employee verbally. A more direct form of feedback would be when the system automatically alerts an employee of an unsafe act via a real-time physical stimulus, such as a buzzer. Either way, the employee receives feedback about his actions and can correct them in the future.

At step 813, the insured company notifies the insurance company about the policies that they have instituted to promote safe behavior. Based on this alone, and without receiving the actual data, insurance company may grant discounts to the insured company at step 817.

Alternatively, the insured company may transmit the actual data to the insurance company at step 815. In this case, the insurance company may perform its own safety evaluation of the data and grant discounts based on the evaluation outcomes at step 819. The insurance company or the insured company may also hire a third party service to perform the evaluation.

In deciding to alter the terms of the insurance policy, the insurance company, or the third party evaluator, may compare the safety performance, as determined from the sensor data, of the insured company to an industry baseline. If the safety performance of the insured company is better than the industry baseline, the insurance company then alters the terms of the policy favorably.

In another scenario, the safety performance of the insured company is compared to its previous performance. For example, if the safety performance of the company improves over its past performance, then the insurance company may award discounts in the premium.

This safety evaluation and feedback system may operate continuously or at certain intervals. The process may repeat itself and lead to new adjustments in insurance policy terms and new feedback may be provided to the employees and the company. A sensor enhanced evaluation system is advantageous because it allows safety improvements at the insured company to be reflected in the policy on a more immediate time basis.

Figure 9:
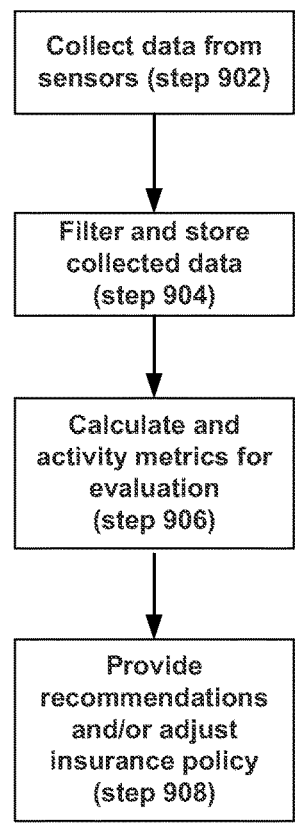
FIG. 9 is a flowchart depicting a process for providing recommendations and/or insurance adjustments based on collected sensor data, according to an embodiment of the invention.

FIG. 9 is a flowchart depicting a process 900 for providing recommendations and/or insurance adjustments based on collected sensor data, according to one embodiment of the invention. Process 900 may be used in healthcare environments as described in FIG. 5, and/or in workplace environments as described in FIG. 1, to monitor injured employees that are recovering.

In step 902, movement/activity data is collected from sensors worn on the body of an employee, worker, or patient, such as sensors 123 (FIGS. 1, 5). In some embodiments, the data are collected and/or analyzed by an activity evaluation module, similar to the safety evaluation module discussed above in relation to FIG. 1. In some embodiments, the activity evaluation module collects raw data directly from the sensors 123. Optionally, the raw data from the sensors 123 is preprocessed before being provided to the activity evaluation module, either by the sensors 123 themselves or another preprocessing device. The movement/activity data may include data indicative of horizontal and/or vertical body position, turning and/or twisting of the body, or sitting/standing postures.

In step 904, the collected sensor data is then filtered to remove unwanted noise, for example via a low-pass filter, and then stored in persistent data storage such as database 129 or data storage 104 (FIGS. 1, 5). Activity metrics or other parameters indicative of movement and activity, such as body movement, body orientation, frequency of movement, duration of movement, movement distance, and calories expended, may then be calculated and used to provide an activity or recovery evaluation in step 906. For example, body movement and orientation over time can be determined with data collected from one or more 3-axis accelerometers. In some embodiments, sensor data may be coupled with user demographic information such as height, age, weight, and/or stride length to estimate a user's activity level.

In one embodiment, the body position/orientation of a user such as an employee or a patient may be determined by calculating the angle of the body on three axes-X, Y, and Z. To calculate the body angle, the worn sensors are first calibrated based on their attachment point(s) to the user's body. A first baseline angle is then determined with the user in a predetermined posture, such as lying down or standing up. This first baseline angle is then stored, and may be compared with other angle measurements taken over time. In one embodiment, the angle measurements are made with one or more 3-axis accelerometers, and may be augmented with data from additional sensors such as gyroscopes, which measure the rotation about one or more axes. For example, in an embodiment with an analog accelerometer and a 10-bit analog-to-digital converter (ADC), the following calculations is used to measure user body angle:
1. Capture the output from the three channels of the accelerometer and express as a number from 1-1023.
2. Convert the output into voltage values for each axis:
   a. VoltsRx=adcRx*Vref/1023,
   b. VoltsRy=adcRy*Vref/1023,
   c. VoltsRz=adcRz*Vref/1023,
where Vref is the reference voltage for the accelerometer.
3. Calculate the signed voltage value by determining the shift from zero acceleration:
   a. deltaVoltsRx=VoltsRx-VzeroG,
   b. deltaVoltsRy=VoltsRy-VzeroG,
   c. deltaVoltsRz=VoltsRz-VzeroG,
where VzeroG is the voltage at zero acceleration for the accelerometer.
4. Calculate the angle:
   a. Axr-arccos (Rx/R)
   b. Ayr-arccos (Ry/R)
   c. Azr-arccos (Rz/R)

Other movement/activity metrics may also be measured. For example, frequency of movement may be determined based on time series data measured by worn accelerometers and/or sensors. If the time series data for a particular user shows that the user experiences a series of acceleration events over time, then the number of acceleration events may be combined with measurements of time to result in a movement/activity frequency measurement. Duration of movement may be measured by performing a weighted average of measured movements/activity over time to differentiate between active and sedentary periods. Movement distance may be approximated from accelerometer data via the following calculations:

velocity final=velocity initial+acceleration*time    1.

distance=velocity final*time−0.5*acceleration*time    2.

In certain embodiments, data indicative of movement or activity below particular thresholds is disregarded. For example, small movements such as fidgeting or brief movements such as stretching may not be included in the determination of activity metrics. Estimated calorie expenditure, which may be indicative of activity level, may be determined as follows:

Men: C/min=(−55.0969+0.6309*heart rate+ 0.1988*weight+0.2017*age)/4.184 (weight is in kg);

Women: C/min=(−20.4022+0.4472*heart rate+ 0.1263*weight+0.074*age)/4.184 (weight is in kg), where heart rate may be directly measured or estimated based on age, weight, and activity level.

After the movement/activity metrics have been measured, recommendations or insurance policy adjustments based on the metrics may be provided in step 908. For example, in a healthcare environment, monitored movement/activity metrics may be used to provide recommendations for loss-control purposes, such as patient intake decisions and/or determinations of if bedridden patients are being moved, shifted, or turned sufficiently often, as described above in relation to FIGS. 5 and 6. In some embodiments, collected sensor data is used for loss control, exposure management, insurance risk evaluation, assessment, and rating, as well as underwriting and/or claims management workflows. In one embodiment, collected movement/activity metrics for patients at a healthcare facility is used to evaluate risks associated with the patients and/or the healthcare facility, and/or is used to adjust insurance policies for patients and/or the healthcare facility. For example, if sensor data for bedridden patients at a healthcare facility indicates that the caregiver-initiated patient movements meet or exceed prescribed movement thresholds, such as frequency and/or amount, the healthcare facility may receive a discount on its insurance.

In some embodiments, the monitored movement/activity metrics may be used for vendor management. For example, the monitored movement/activity metrics of patients at a healthcare facility may be used to evaluate how well a particular the facility/healthcare vendor adheres to prescribed guidelines, as well as how quickly patients at that facility recover. If a particular healthcare facility/vendor consistently meets prescribed guidelines and/or is characterized by quick recovery of its patients, more injured individuals may be referred to that facility/vendor. In certain embodiments, the collected sensor data and movement/activity metrics can also be stored and used to provide proof of adherence to prescribed guidelines for use if malpractice claims are brought against a vendor and/or insurance company.

In some embodiments, the collected information is aggregated at different levels. For example, collected sensor information for a group of individuals under a group benefit/insurance policy may be aggregated so that an insurance company can evaluate the overall risk of the group. Similarly, collected sensor information for a particular healthcare facility/vendor, or even individual caregivers or groups of caregivers in a particular facility, may be aggregated to allow for risk evaluation, for example for evaluating risks associated with general liability/professional liability and/or medical malpractice coverage. For example, an insurance company providing professional liability insurance to a particular caregiver may aggregate and analyze movement/activity information for patients under that caregiver's supervision to evaluate the risk associated with that caregiver. In some embodiments, the determination of whether a particular insurance policy is to be renewed is based on the movement/activity information.

As yet another example, the movement/activity level and/or the lifting behavior of an injured employee that has returned to work may be monitored to prevent re-injury and to speed recovery. In this example, personalized activity and/or lifting thresholds, such as the number of allowable lifts per day, the amount or degree of bending allowable, allowable postures, or allowable weight limits may be established for the injured employee, and as the employee approaches or reaches the established thresholds, the employee may be notified in real-time. In some embodiments, the occupational health and claims case worker responsible for the employee is also be notified. In some embodiments, the notifications to the injured employee and/or the case worker(s) includes immediate feedback upon detection of an undesired lifting behavior (e.g., warning the employee when he/she is about to engage in dangerous/unsafe lifting), summaries of lifting behavior/activities for a period of time (e.g., lifting behavior for the past eight hours), and/or notification of conformance with a recovery plan (e.g., whether the employee has or has not exceeded the maximum allowable lifts, and if so, by how much). In some embodiments, caregivers, case workers, or other relevant personnel can input the personalized activity/lifting thresholds by a user interface similar to user interface module 105 (FIG. 1). Similarly, the notifications to the injured employee and/or the case worker(s) can be presented on the user interface.

In some embodiments, the method for evaluating and improving workplace safety described in FIG. 8 may be modified to use sensor data collected in step 902 to evaluate and improve workplace health, assist in the return-to-work recovery of injured employees, and/or assist in loss-control of health and injury claims. For example, the sensor data may be combined with static data (step 805, FIG. 8) and/or third party data (step 803, FIG. 8) and analyzed, processed, and/or aggregated (step 807, FIG. 8) to provide activity and/or lifting evaluations. The insured entity may institute policies to promote healthy activity based on the data (or to improve patient movement frequency, for healthcare facilities) (step 809, FIG. 8), and may receive discounts or other favorable insurance policy adjustments from insurance companies providing insurance to the entity.

Figure 10:
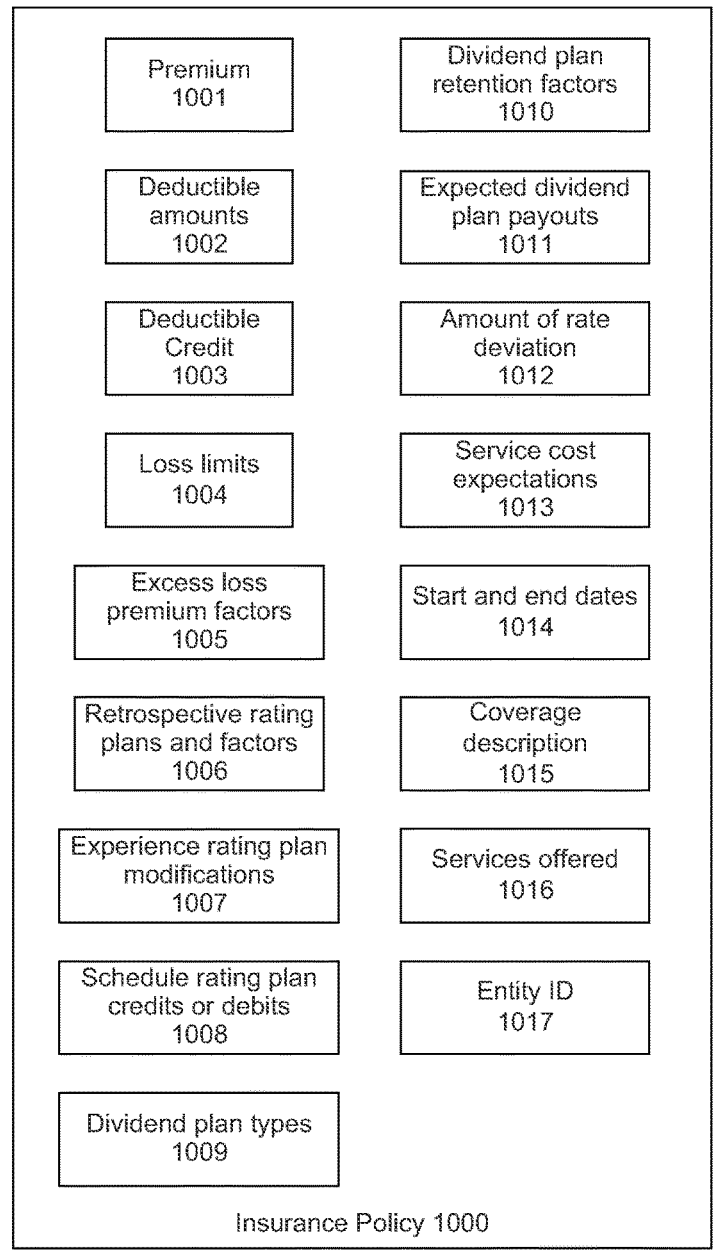
FIG. 10 is a schematic diagram of the terms of an insurance policy.

FIG. 10 shows exemplary insurance policy terms that can be adjusted in the present system. Insurance policy 1000 is characterized by terms 1001-1017. In response to a safety or recovery evaluation associated with an insured entity, some of the terms 1001-1017 of the insurance policy are adjusted to reflect the evaluation. For example, a favorable evaluation may lead to a decrease in premium 1001 and deductible amount 1002. An unfavorable evaluation may lead to an increase in premium 1001. The deductible credit 1003, loss limit 1004, excess loss premium factors 1005, retrospective rating plans and factors 1006, experience rating plan modifications 1007, schedule rating plan credits or debits 1008, dividend plan types 1009, dividend plan retention factors 1010, expected dividend plan payouts 1011, amount of rate deviation 1012, service cost expectations 1013, start and end dates 1014, coverage description 1015, services offered 1016, entity ID 1017, and other policy terms may be altered in a similar manner. In some embodiments, the determination of whether to renew an insurance policy covering an insured entity is based on the evaluation.

What is claimed is:

1. An activity evaluation system comprising:
a communications device configured to receive (1) sensor data based on at least one sensor configured to monitor activity of an individual associated with and distinct from a covered entity, and (2) an activity evaluation for the individual; and
a computer hardware server, operated by a risk management entity and in communication with the communications device, configured to adjust data corresponding to a parameter of a risk management policy covering the covered entity based on the sensor data and the activity evaluation, wherein the computer hardware server is configured to adjust the data corresponding to the parameter so as to provide an adjustment favorable to the covered entity responsive to the activity evaluation being indicative of desired activity by the individual;
wherein the computer hardware server is further configured to:
determine, based on the sensor data, whether the individual has conformed with activity guidelines applicable to the individual; and
responsive to a negative determination that the individual has conformed with the activity guidelines, transmit an alert to a computing device of the covered entity.

2. The system of claim 1, wherein the computer hardware server is further configured to:
generate, based at least in part on the activity evaluation, data indicative of a risk management recommendation comprising a loss-control recommendation for one or both of the covered entity and a healthcare provider; and
output, by a communications system, an electronic communication having the data indicative of the risk management recommendation to one or both of the covered entity and the healthcare provider.

3. The system of claim 1, wherein the computer hardware server being configured to transmit the alert to the covered entity comprises the computer hardware server being configured to transmit the alert to one or more of a local computer, an audio buzzer at a workplace configured to output an audio signal responsive to receipt of the alert, a flashing light at the workplace configured to flash responsive to receipt of the alert, and a vibrating device worn by an employee configured to vibrate responsive to receipt of the alert.

4. The system of claim 1, wherein the sensor data comprises one or both of raw sensor data directly from the at least one sensor configured to monitor activity of the individual and preprocessed sensor data based on the raw sensor data from the at least one sensor.

5. The system of claim 1, wherein the sensor data comprises preprocessed sensor data including data indicative of one or more of body movement, body orientation, frequency of movement, duration of movement, movement distance, and calories expended, calculated based upon raw sensor data.

6. The system of claim 1, wherein the at least one sensor comprises one of a sensor worn by the individual, a sensor on a piece of equipment, a gyroscopic sensor, an accelerometer, a motion sensor, a pressure sensor, a chemical sensor, and a GPS sensor.

7. The system of claim 1, wherein the at least one sensor comprises a three-axis accelerometer, and wherein the computer hardware server is further configured to:
  calculate a frequency of movement based on a series of the sensor data received from the three-axis accelerometer; and
  calculate a duration of movement based on a weighted average of movements over time identified in the series of the sensor data;
  wherein the computer hardware server is configured to adjust the data corresponding to the parameter of the risk management policy based upon the calculated frequency of movement and the calculated duration of movement.

8. The system of claim 1, wherein the individual associated with and distinct from the covered entity comprises an employee of the covered entity;
  wherein the sensor data comprises one or more of RFID scanner data, GPS data, and photo recognition data corresponding to the employee;
  wherein the activity guidelines comprise workplace safety guidelines at a workplace of the covered entity; and
  wherein determining whether the individual has conformed with the activity guidelines comprises determining a number of times the employee has accessed hazardous areas at the workplace.

9. A method for evaluating activity of an individual associated with and distinct from a covered entity, comprising:
  receiving by a hardware server, the hardware server comprising at least one processor, (1) sensor data based on at least one sensor monitoring activity of the individual associated with and distinct from the covered entity, and (2) an activity evaluation for the individual;
  adjusting, by the hardware server, data corresponding to a risk management policy covering the covered entity based on the sensor data and the activity evaluation, the adjusting comprising adjusting data corresponding to at least one parameter so as to provide an adjustment favorable to the covered entity responsive to the activity evaluation being indicative of desired activity by the individual;
  determining, based on the sensor data, whether the individual has conformed with activity guidelines applicable to the individual; and
  responsive to a negative determination that the individual has conformed with the activity guidelines, transmit an alert to a computing device of the covered entity.

10. The method of claim 9, further comprising:
  generating, by the hardware server, based at least in part on the activity evaluation, data indicative of a risk management recommendation comprising a loss-control recommendation to one or both of the covered entity and a healthcare provider; and
  outputting, by an output device, the data indicative of the risk management recommendation to one or both of the covered entity and the healthcare provider.

11. The method of claim 10, wherein the loss-control recommendation comprises one or more of a patient intake decision for the individual, an initial diagnosis for the individual, care instructions for the individual, a patient progress determination for the individual, a determination of sufficient activity for the individual, and a determination of activity conformance for the individual.

12. The method of claim 9, wherein the individual associated with and distinct from the covered entity comprises a patient at a health care facility;
  wherein the activity guidelines comprise prescribed motion for the patient;
  wherein determining whether the individual has conformed with the activity guidelines comprises determining, by the hardware server based on the sensor data, whether the prescribed motion for the patient has been performed; and
  wherein transmitting the alert to the covered entity comprises, responsive to a negative determination that the prescribed motion for the patient has been performed, transmitting the alert to a user terminal at the health care facility.

13. The method of claim 12, wherein the sensor data comprises data indicative of one or more of horizontal body positions, vertical body positions, turning of a body, twisting of a body, sitting postures, and standing postures calculated based upon raw sensor data.

14. The method of claim 9, wherein the individual associated with and distinct from the covered entity comprises an employee of the covered entity returning from an injury;
  wherein the activity guidelines comprise a recovery plan prescribed for the employee;
  wherein determining whether the individual has conformed with the activity guidelines comprises determining, by the hardware server based on the sensor data, whether the employee has conformed with the recovery plan prescribed for the employee; and
  wherein transmitting the alert to the covered entity comprises, responsive to a negative determination that the employee has conformed with the recovery plan, transmitting the alert to a local computer at the covered entity.

15. The method of claim 9, wherein the individual associated with and distinct from the covered entity comprises an employee of the covered entity;
  wherein the activity guidelines comprise workplace safety guidelines at a workplace of the covered entity;
  wherein determining whether the individual has conformed with the activity guidelines comprises determining, by the hardware server based on the sensor data, whether the employee has conformed with the workplace safety guidelines at the workplace of the covered entity; and
  wherein transmitting the alert to the covered entity comprises, responsive to a negative determination that the employee has conformed with the workplace safety guidelines, transmitting the alert to one of more of a local computer at the workplace of the covered entity, an audio buzzer at the workplace configured to output an audio signal responsive to receipt of the alert, a flashing light at the workplace configured to flash responsive to receipt of the alert, and a vibrating device worn by the employee configured to vibrate responsive to receipt of the alert.

16. The method of claim 9, wherein adjusting, by the hardware server, the data corresponding to the at least one parameter of the risk management policy covering the covered entity is further based on demographic data about the individual comprising one or more of height data, age data, weight data, and stride length data corresponding to the individual; and
  wherein the hardware server being configured to transmit the alert to the covered entity comprises the hardware server being configured to transmit the alert to one or more of a local computer, an audio buzzer at a workplace configured to output an audio signal responsive to receipt of the alert, a flashing light at the workplace configured to flash responsive to receipt of the alert, and a vibrating device worn by an employee configured to vibrate responsive to receipt of the alert.

* * * * *